United States Patent
Hacohen et al.

(10) Patent No.: US 8,802,924 B2
(45) Date of Patent: Aug. 12, 2014

(54) POLYUNSATURATED FATTY ACID ELONGASE

(75) Inventors: Zvi Hacohen, Omer (IL); Inna Khozin Goldberg, Sde-Boker (IL); Rivka Ofir, DN Arava (IL); Iskandarov Umidjon, Sde-Boker (IL)

(73) Assignee: Ben Gurion University of the Negev Research and Development Authority, Beer Sheva (IL)

( * ) Notice: Subject to any disclaimer, the term of this patent is extended or adjusted under 35 U.S.C. 154(b) by 437 days.

(21) Appl. No.: 13/132,939

(22) PCT Filed: Nov. 26, 2009

(86) PCT No.: PCT/IL2009/001117
§ 371 (c)(1),
(2), (4) Date: Aug. 10, 2011

(87) PCT Pub. No.: WO2010/067352
PCT Pub. Date: Jun. 17, 2010

(65) Prior Publication Data
US 2011/0289628 A1   Nov. 24, 2011

Related U.S. Application Data

(60) Provisional application No. 61/193,589, filed on Dec. 9, 2008.

(51) Int. Cl.
| | | |
|---|---|---|
| C12N 15/87 | (2006.01) | |
| C12N 15/82 | (2006.01) | |
| C12N 15/00 | (2006.01) | |
| C12N 15/74 | (2006.01) | |
| C12N 9/00 | (2006.01) | |
| C12P 21/06 | (2006.01) | |
| C12P 7/64 | (2006.01) | |
| C07H 21/04 | (2006.01) | |
| A61K 38/43 | (2006.01) | |

(52) U.S. Cl.
USPC .......... 800/281; 800/295; 435/69.1; 435/134; 435/183; 435/320.1; 435/468; 424/94.1; 536/23.7

(58) Field of Classification Search
None
See application file for complete search history.

(56) References Cited

U.S. PATENT DOCUMENTS

| | | | | |
|---|---|---|---|---|
| 2005/0089879 | A1* | 4/2005 | Feussner et al. | 435/6 |
| 2005/0214761 | A1* | 9/2005 | Lerchl et al. | 435/6 |
| 2006/0024404 | A1* | 2/2006 | Kyle | 426/2 |

OTHER PUBLICATIONS

Bigogno et al 2002 Phytochemistry 60: p. 497-503.*
Khozin-Goldberg et al 2002 Journal of Phycology 38: p. 991-994.*

* cited by examiner

*Primary Examiner* — David T Fox
*Assistant Examiner* — Matthew Keogh
(74) *Attorney, Agent, or Firm* — Roach Brown McCarthy & Gruber, P.C.; Kevin D. McCarthy

(57) ABSTRACT

An isolated protein which is at least partially encoded by a polynucleotide sequence encoding a novel elongase is provided together with a composition which includes the isolated protein. A transgenic plant or a transgenic seed transformed by a polynucleotide encoding a protein which is at least partially encoded by a novel elongase is also provided. The invention also includes a process for making a very long-chain polyunsaturated fatty acid in a transformed cell or plant expressing the isolated protein which is at least partially encoded by a polynucleotide sequence encoding a novel elongase.

20 Claims, 7 Drawing Sheets

```
PiELO1    --------------------------------MA-------LTAAWHKYDAIVSRFVFDG  21
OtELO1    --------------------------------MSGLRAPNFLHRFWTKWDYAISKVVFTC  28
MpELO1    -----------------------------------MEAYEMVDSFVSKTVFET         18
PpELO1    -----------------------------------MEVVERFYGELDGKVSQG          18
MpELO2    MATKSGSGLLEWIAVAAKMKQARSSPEGEIVGGNRMGSGNGAEWTTSLIHAFLNATNGKS   60
ThrELO1   ----------------------------------MDVVEQQWRRFVDAVDNGIVEF      22
                                                   :  .

PiELO1    LRR-------------------VGLQEIQGHPSVITAHLPFIASPTPQVTFVLAYLLIVV   62
OtELO1    AD--------------------SFQWDIGPVSSSTAHLPAIESPTPLVTSLLFYLVTVF   67
MpELO2    ------------------LQRLRG--GVVLTES-AITKGLPCVDSPTPIVLGLSSYLTFVF  58
PpELO1    ------------------VNALLGSFGVELTDT-PTTKGLPLVDSPTPIVLGVSVYLTIVI  60
MpELO2    GGASKVRPLEERIGEAVFRVLEDVVGVDIRKPNPVTKDLPMVESPVPVLACISLYLLVVW   120
ThrELO1   --------------------MEHEEPNKLNEGK-LSTSTEEMMALIVGYLAFVV        55
                                             *.   :   :   **    *

PiELO1    CGVAALRTRKSSAPREDPAWLRLLVQAHNLVLISLSAYMSSAACYYAWKYGYRFWGTNYS   122
OtELO1    LWYGRL-TRSSDKKIREPTWLRRFIICHNAFLIVLSLYMCLGCVAQAYQNGYTLWGNEFK   126
MpELO1    LGLIVIKSLDLKPRSKEPAILNLFVIFHNFVCFALSLYMCVGIVRQAILNRYSLWGNAYN   118
PpELO1    GGLLWIKARDLKPRASEPFLLQALVLVHNLFCFALSLYMCVGIAYQAITWRYSLWGNAYN   120
MpELO2    LWSSHIKASGQKPRKEDPLALRCLVIAHNLFLCCLSLFMCVGLIAAARHYGYSVWGNYYR   180
ThrELO1   LGSAFMKAFVDK-----PFELKFLKLVHNIFLTGLSMYMATECARQAYLGGYKLFGNPME  110
               :   :     *  *. :   ** **  :**  .       *      .:*.

PiELO1    P----KERDMGGLIYTFYMSKYYEFVDTLIMLLKGKVEQVSFLHVYHHASISTIWWAIAY   178
OtELO1    A----TETQLALYIYIFYVSKYYEFMDTYIMLLKNNLRQVSFLHVYHHSEISFIWWIIAR   182
MpELO1    P----KEVQMGHLLYIFYMSKYYEFMDTVIMLKRNTRQILVLHVYHHASTSFIWWIIAY   174
PpELO1    P----KHKEMAILVYLFYMSKYVEFMDTVIMILKRSTROTSFLHVYHHSSISLIWWAIAH   176
MpELO2    E----REPAMNLLIYVFYMSKLYEFMDTAIMLFRRNLRQVTYLHVYHHASTAMIWWIICY   236
ThrELO1   KGTESHAPGMANIIYIFYVSKFLEELDIVFMILGKKWKQLSFLHVYHHASISFIWGIIAR   170
                   :  ** ::** *** :** :::   .:*::  :::::*:*: ** *.

PiELO1    VAPGGDAWYCCFINSIVHVIMYTYYLLATLLGKDAKARRKYLWWGRYLTQFQMFQFVTMM  238
OtELO1
RAPGGDAYFSAALNSWVHVCMYTYYLLSTLIGKEDPKRSNYLWWGRHLTQMQMFQFFFNV  242
MpELO1    HAPGGEAYFSAALNSGVHVIMYLYYLLAATLGKNEKARRKYLWWGKYLTQLQMFQFVLNM  234
PpELO1    HAPGGEAYWSAALNSGVHVIMYAYYFLAACLRSSPKLKNKYLFWGRYLQFQMFQFMLNL   236
MpELO2    RFPGADSYFSAAFNSCHVAMYIYYLLAATVARDEKRRRKYLFWGKYLTTOMLQFLSFI    296
ThrELO1   FAPGGDAYFSTILNSSVHVIYGYYASTTLGYTFMRPLR------PYILTQFTQFMAMV   224
             **.::::.   :**::**  :* **   ::         ::*  :*:  ** .  :

PiELO1    LEAAYTWA-YSPYPKFLSKLLFFYMITLLALFANFYAQKHGSS-----RAAKQKLQ     288
OtELO1    LQALYCAS-FSTYPKFLSKILLVYMMSLLGLFGHFYYSKHIAA-----AKLQKKQQ     292
MpELO1    IQAYYDIKNNSPYPQFLIQILFYYMISLLALFGNFYVHKYVSAPAKPAKIKSKKAE     290
PpELO1    VQAYYDMKTNAPYPQWLIKILFYYMISLLFLFGNFYVQKYIKP--SDGKQKGAKTE     290
MpELO2    GQAIYAMWKFEYYPKGFGRMLFFYSVSLLAFFGNFFVKKYSNA----SQPKTVKVE     348
ThrELO1   VQSVYDYYNPCDYPQPLVKLLFWYMLTMLGLFGNFFVQQYLKP----KAPKKQKTI     276
          ::  *      **:  ::*: * :::*  :*..:*   ::              *

FIG 1
```

```
      1 atggcattga cggcggcctg gcacaagtac gacgctatcg ttagtcgctt
tgttttcgat
     61 ggcttgcgca gggttggcct gcaagagatt caaggccacc cctcggtgat
caccgcccac
    121 cttcccttca tagcctcccc aacgccacaa gtgacgttcg tgctggccta
tctgctgatt
    181 gttgtctgcg gggttgccgc tctgcgtacg agaaagtcgt ccgcacctcg
cgaggatccg
    241 gcgtggctgc gactgcttgt gcaagcgcac aacttggtgc taatcagcct
tagcgcctac
    301 atgtcctctg ccgcctgcta ctatgcttgg aaatacggct ataggttttg
gggcacaaac
    361 tatagcccca aggagcggga catgggaggg ctcatctata cctttacgt
gtccaagctg
    421 tacgagtttg tggatacgct gatcatgctg tcaagggca aggtggagca
ggtttctttt
    481 ttgcacgtct accaccacgc ttccatatcc acgatctggt gggcaatcgc
atacgtcgca
    541 cctggtggtg acgcctggta ctgctgcttc ctgaactcgc tggtccacgt
actcatgtac
    601 acatactacc tgcttgcgac gctgctggga aaggacgcca aggcgcggcg
caagtatttg
    661 tggtggggac gctacctcac tcagttccag atgttccagt ttgtgacgat
gatgctcgag
    721 gcagcgtaca cttgggccta ctctccctac cccaagtttt tatcaaagct
gctgttcttt
    781 tacatgatca ctctgttggc cctgtttgca aacttctatg cacagaagca
tggcagcagc
    841 cgggcagcca agcaaaagct gcagtaa
```

/translation="MALTAAWHKYDAIVSRFVFDGLRRVGLQEIQGHPSVITAHLPFI

ASPTPQVTFVLAYLLIVVCGVAALRTRKSSAPREDPAWLRLLVQAHNLVLISLSAYMS

SAACYYAWKYGYRFWGTNYSPKERDMGGLIYTFYVSKLYEFVDTLIMLLKGKVEQVSF

LHVYHHASISTIWWAIAYVAPGGDAWYCCFLNSLVHVLMYTYYLLATLLGKDAKARRK

YLWWGRYLTQFQMFQFVTMMLEAAYTWAYSPYPKFLSKLLFFYMITLLALFANFYAQK

HGSSRAAKQKLQ"

Fig.6

[Myrmecia incisa]
MALTAAWHKYDAIVSRFVFDGLRRVGLQEIQGHPSVITAHLPFIASPTPQ 50
[Parietochloris incisa]
MALTAAWHKYDAIVSRFVFDGLRRVGLQEIQGHPSVITAHLPFIASPTPQ 50

**************************************************

[Myrmecia incisa]
VTFVLAYLLIVVCGVAALRTRKSSAPREDPAWLRLLVQAHNLVLISLSAY 100
[Parietochloris incisa]
VTFVLAYLLIVVCGVAALRTRKSSAPREDPAWLRLLVQAHNLVLISLSAY 100

**************************************************

[Myrmecia incisa]
MSSAACYYAWKYGYRFWGTNYSPKERDMGGLIYTLYVSKLYEFVDTLIML 150
[Parietochloris incisa]
MSSAACYYAWKYGYRFWGTNYSPKERDMGGLIYTFYVSKLYEFVDTLIML 150

**************************************:***********

[Myrmecia incisa]
LKGKVEQVSFLHVYHHASISTIWWAIAYVAPGGDAWYCCFLNSPVHVLMY 200
[Parietochloris incisa]
LKGKVEQVSFLHVYHHASISTIWWAIAYVAPGGDAWYCCFLNSLVHVLMY 200

******************************************  ****

[Myrmecia incisa]
TYYLLATLLGKDAKARRKYLWWGRTLTQFQMFQFVTMMLEAAYTWAYSPY 250
[Parietochloris incisa]
TYYLLATLLGKDAKARRKYLWWGRMLTQFQMFQFVTMMLEAAYTWAYSPY 250
                        *********************
***********************

[Myrmecia incisa]
PKFLSKLLFFYMITLLALFANFYAQKHGSSRAAKQKEQ 288
[Parietochloris incisa]
PKFLSKLLFFYMITLLALFANFYAQKHGSSRAAKQKLQ 288

POLYUNSATURATED FATTY ACID ELONGASE

CROSS-REFERENCE TO RELATED APPLICATIONS

This application is a National Phase Application of PCT International Application No. PCT/IL2009/001117, International Filing Date Nov. 26, 2009, claiming priority of U.S. Provisional Patent Application No. 61/193,589, filed Dec. 9, 2008.

FIELD OF INVENTION

This invention is directed to, inter alia, the identification of a cDNA encoding for a *P. incisa* polyunsaturated fatty acid elongase (PiELO1) and methods of making and utilizing the same.

BACKGROUND OF THE INVENTION

The very long-chain polyunsaturated fatty acid (VLC-PUFA), arachidonic acid (ARA, 20:4ω6), is a component of neuron tissues such as brain and retina cells and an important component of the human diet. ARA is a primary substrate for the biosynthesis of eicosanoids, including the 2-group prostaglandins, 4-group leukotrienes, thromboxanes and lipoxins that serve as biological effectors involved in inflammatory and immune responses and cell signaling. Being an important and dominant VLC-PUFA in human breast milk, ARA needs to be externally supplied for normal development of preterm babies if they are not breast-fed. Due to its beneficial properties there is a growing interest in the production of ARA for baby formulae. At present, the major commercial source of ARA is the filamentous fungus *Mortierella alpina*.

Microalgae are the most efficient producers and one of the richest sources of VLC-PUFAs. Furthermore, algae can be used as sources of genes for the implementation of VLC-PUFA biosynthesis in genetically engineered oil crops. The genetic information on enzymes involved in the biosynthesis of VLC-PUFA in some algae led to in vivo applications of VLC-PUFA production in seed oil. The gene pool of the green freshwater microalga *Parietochloris incisa* (Trebouxiophyceae) is of special interest since it is the only known microalga able to accumulate extraordinary high amounts of ARA-rich triacylglycerols (TAG). When *P. incisa* is cultivated under nitrogen starvation, the condition triggering storage oil accumulation, ARA constitutes about 60 percent of total fatty acids (TFA) and over 95 percent of cellular ARA is deposited in TAG in cytoplasmic lipid bodies.

The biosynthesis of VLC-PUFAs in algae follows various pathways initiating from oleic acid exported from the chloroplast and employing polar extraplastidial lipids. In the ω6 and ω3 pathways, linoleic acid (LA; 18:2ω6) and α-linolenic acid (ALA; 18:30ω3) are successively converted by Δ6 desaturase, Δ6 elongase and Δ5 desaturase to ARA and eicosapentaenoic acid (EPA, 20:5ω3), respectively. E.g., In *P. incisa*, as well as the red microalga *Porphyridium cruentum*, ARA biosynthesis proceeds via the ω6 pathway.

Unusual elongations and desaturations leading to the biosynthesis of VLC-PUFA have been reported in the marine haptophyte *Isochrysis galbana* and the fresh water euglenophyte *Euglena gracilis*. In the alternative route, elongation of 18:2ω6 and 18:3ω3 by a C18-Δ9-specific fatty acid elongase to the respective C20 intermediates precedes sequential Δ8 and Δ5 desaturations to ARA and EPA, respectively. It is assumed that in *E. gracilis* EPA produced by the ω3-Δ8 pathway is further Δ4 desaturated and finally elongated to docosahexaenoic acid (DHA, 22:6ω3).

Fatty acid elongation is a multi-step process involving four sequential enzymatic reactions: rate limiting condensation (of malonyl-CoA and acyl-CoA), reduction, dehydration and enoyl reduction. Only the expression of the condensing enzyme component is required to reconstitute elongase activity in the heterologous host; there is no requirement for the co-expression of any other component of the elongase complex. Multiple microsomal elongation systems with different specificities to the acyl chain length exist in various organisms. Recent studies have identified and characterized PUFA-specific elongases, responsible for the elongation of PUFA in mammals, fish, algae, lower plants and fungi. The elongation of 18:3ω6 to 20:3ω6, the immediate precursor of ARA, was shown to be the rate limiting step in ARA biosynthesis in *M. alpina*. Functional expression of the PUFA elongase condensation component in yeast revealed enzymes of various specificities for C18 and C20 acyl substrates. Thus, two types of PUFA elongases engaged in DHA biosynthesis were cloned from the green microalga *Ostreococcus tauri* and the diatom *Thalassiosira pseudonana*: OtELO1 and TpELO1 are Δ6 C18-PUFA specific and involved in the elongation of the 18:3ω6 and 18:4ω3, while OtELO2 and TpELO2 are Δ5 C20-PUFA elongases involved in the elongation of 20:5ω3. Bifunctional PUFA elongases able to elongate both Δ6 and Δ5 PUFA, as well as elongases of wide substrate specificity utilizing both C20 and C22 PUFA substrates, were isolated from aquatic animals.

SUMMARY OF THE INVENTION

In one embodiment, the present invention provides an isolated protein comprising a peptide, wherein the peptide comprises an amino acid sequence set forth in SEQ ID NO: 1.

In another embodiment, the present invention further provides a composition comprising an isolated protein comprising a peptide, wherein the peptide comprises an amino acid sequence set forth in SEQ ID NO: 1.

In another embodiment, the present invention further provides an isolated polynucleotide comprising a coding portion encoding a protein comprising a peptide, wherein the peptide comprises an amino acid sequence set forth in SEQ ID NO: 1.

In another embodiment, the present invention further provides an isolated polynucleotide comprising a nucleic acid sequence set forth in SEQ ID NO: 2.

In another embodiment, the present invention further provides a transgenic plant or a transgenic seed transformed by a polynucleotide comprising a coding portion encoding a protein comprising a peptide, wherein the peptide comprises an amino acid sequence set forth in SEQ ID NO: 1.

In another embodiment, the present invention further provides a method of producing very long-chain polyunsaturated fatty acid (VLC-PUFA) in a plant or a plant cell, comprising the step of transforming a plant or a plant cell with a polynucleotide comprising a coding portion encoding a protein comprising a peptide, wherein the peptide comprises an amino acid sequence set forth in SEQ ID NO: 1.

In another embodiment, the present invention further provides a method of enhancing oil storage, arachidonic acid accumulation, or a combination thereof in a plant cell, comprising the step of transforming a plant cell with a polynucleotide comprising a coding portion encoding a protein comprising a peptide, wherein the peptide comprises an amino acid sequence set forth in SEQ ID NO: 1.

BRIEF DESCRIPTION OF THE DRAWINGS

FIG. 1. Depicts the amino acid sequence of *P. incisa* PiELO1 aligned with its closest homologs using CLUSTAL W (1.83) multiple sequence alignment program (default). Conserved motifs characteristic of PUFA elongase sequences are highlighted. GeneBank accession numbers for the sequences are OtELO1 (*O. tauri*, AAV67797), MpELO1 (*M. polymorpha*, AAT85662), PpELO1 (*P. patens*, AAL84174), MpELO2 (*M. polymorpha*, BAE71129), and ThrELO1 *Thraustochytrium* sp. FJN-10, ABC18313).

FIG. 6. Depicts *Parietochloris incisa* polyunsaturated fatty acid elongase (ELO1) gene, complete cds, 867 bp and amino acid sequence.

FIG. 7. Depicts the cDNA sequence for the putative PUFA Elongase of *Myrmecia incisa* with 98% similarity to *P. incisa*. Shown are details and alignment for deduced amino acid sequences for both elongases. As shown the sequences differ in five amino acid residues (highlighted in grey) located in conserved regions important for functional activity for the enzyme. The LOCUS ACF60496 comprises 288 aa, linear PLN 29-JUL-2008, DEFINITION polyunsaturated fatty acids elongase [*Myrmecia incisa*].

DETAILED DESCRIPTION OF THE INVENTION

Figure 2:
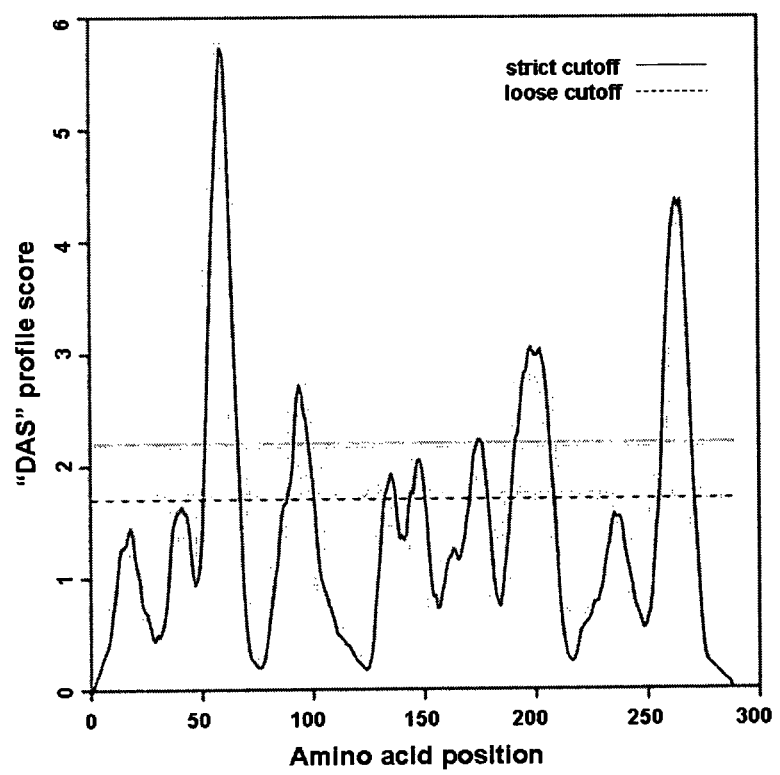
FIG. 2. Is a hydropathy plot of the amino acid sequence of PiELO1. The lower dashed line and the upper line represent the loose transmembrane region cutoff and the strict transmembrane region cutoff, respectively.

In one embodiment, the present invention provides an isolated protein comprising a peptide. In another embodiment, the present invention provides that the isolated protein is a polypeptide. In another embodiment, the present invention provides a peptide comprising the amino acid sequence:

```
                                        (SEQ ID NO: 1)
MALTAAWHKYDAIVSRFVFDGLRRVGLQEIQGHPSVITAHLPFIASP

TPQVTFVLAYLLIVVCGVAALRTRKSSAPREDPAWLRLLLVQAHNLVL

ISLSAYMSSAACYYAWKYGYRFWGTNYSPKERDMGGLIYTFYVSKLY

EFVDTLIMLLKGKVEQVSFLHVYHHASISTIWWAIAYVAPGGDAWYC

CFLNSLVHVLMYTYYLLATLLGKDAKARRKYLWWGRYLTQFQMFQFV
```

```
TMMLEAAYTWAYSPYPKFLSKLLFFYMITLLALFANFYAQKHGSSRA

AKQKLQ.
```

In another embodiment, the peptide comprises an amino acid sequence that is at least 60% homologous to the amino acid sequence of SEQ ID NO: 1. In another embodiment, the peptide comprises an amino acid sequence that is at least 70% homologous to the amino acid sequence of SEQ ID NO: 1. In another embodiment, the peptide comprises an amino acid sequence that is at least 75% homologous to the amino acid sequence of SEQ ID NO: 1. In another embodiment, the peptide comprises an amino acid sequence that is at least 80% homologous to the amino acid sequence of SEQ ID NO: 1. In another embodiment, the peptide comprises an amino acid sequence that is at least 85% homologous to the amino acid sequence of SEQ ID NO: 1. In another embodiment, the peptide comprises an amino acid sequence that is at least 90% homologous to the amino acid sequence of SEQ ID NO: 1. In another embodiment, the peptide comprises an amino acid sequence that is at least 95% homologous to the amino acid sequence of SEQ ID NO: 1. In another embodiment, the peptide comprises an amino acid sequence that is at least 98% homologous to the amino acid sequence of SEQ ID NO: 1.

In another embodiment, the peptide comprises an amino acid sequence that is at least 60% identical to the amino acid sequence of SEQ ID NO: 1. In another embodiment, the peptide comprises an amino acid sequence that is at least 70% identical to the amino acid sequence of SEQ ID NO: 1. In another embodiment, the peptide comprises an amino acid sequence that is at least 75% identical to the amino acid sequence of SEQ ID NO: 1. In another embodiment, the peptide comprises an amino acid sequence that is at least 80% identical to the amino acid sequence of SEQ ID NO: 1. In another embodiment, the peptide comprises an amino acid sequence that is at least 85% identical to the amino acid sequence of SEQ ID NO: 1. In another embodiment, the peptide comprises an amino acid sequence that is at least 90% identical to the amino acid sequence of SEQ ID NO: 1. In another embodiment, the peptide comprises an amino acid sequence that is at least 95% identical to the amino acid sequence of SEQ ID NO: 1. In another embodiment, the peptide comprises an amino acid sequence that is at least 98% identical to the amino acid sequence of SEQ ID NO: 1.

In another embodiment, the peptide comprises at least a portion of the amino acid shown in SEQ ID. NO: 1. In another embodiment, the peptide is a variant of SEQ ID. NO: 1. In another embodiment, the term "variant" in relation to a certain sequence means a protein or a polypeptide which is derived from the sequence through the insertion or deletion of one or more amino acid residues or the substitution of one or more amino acid residues with amino acid residues having similar properties, e.g., the replacement of a polar amino acid residue with another polar amino acid residue, or the replacement of a non-polar amino acid residue with another non-polar amino acid residue. In all cases, variants must have an elongase function as defined herein.

In another embodiment, the protein as described herein further comprises a leader peptide. In another embodiment, the leader peptide allows the polypeptide to be specifically located or targeted to a target organelle within the cell. In another embodiment, the protein as described herein further comprises a sequence motif responsible for Endoplasmic Reticulum (ER)-retention.

In another embodiment, the present invention provides an isolated PUFA elongase. In another embodiment, the present invention provides an isolated polypeptide comprising a functional long chain polyunsaturated fatty acid (PUFA) elongase. In another embodiment, the present invention provides that the polypeptide has the function of extending the chain length of an 18 carbon PUFA to 20 carbons in length.

In another embodiment, the present invention provides that the isolated protein comprises an elongase activity. In another embodiment, the present invention provides a peptide comprising an elongase activity. In another embodiment, the present invention provides a peptide consisting an elongase activity. In another embodiment, the present invention provides that the peptide is an elongase. In another embodiment, the present invention provides that the elongase is a polyunsaturated fatty acid (PUFA)-specific elongase. In another embodiment, the present invention provides that the elongase elongates 18:3ω6 to 20:3ω6. In another embodiment, the present invention provides that the elongase elongates precursors of arachidonic acid. In another embodiment, the present invention provides that the elongase elongates immediate precursors of arachidonic acid (ARA). In another embodiment, the present invention provides that the elongase is a Δ6 PUFA elongase. In another embodiment, the present invention provides that the protein as described herein is used to elevate PUFA levels in animals, thereby providing a ready source of PUFAs.

In another embodiment, the present invention provides that the elongation of the precursors of arachidonic acid is the rate limiting step in ARA biosynthesis. In another embodiment, the present invention provides that elongase activity is the rate limiting step in ARA biosynthesis. In another embodiment, the expression and/or transcription of the elongase as described herein is up-regulated during nitrogen starvation. In another embodiment, the expression and/or transcription level of the elongase as described herein correlates with the production of ARA precursors.

In another embodiment, the present invention provides an isolated polynucleotide encoding the protein as described herein. In another embodiment, an isolated polynucleotide is an isolated DNA molecule. In another embodiment, the isolated polynucleotide comprises a sequence encoding the peptide as described herein. In another embodiment, the isolated polynucleotide comprises a DNA sequence encoding the peptide as described herein. In another embodiment, the isolated polynucleotide comprises a DNA sequence encoding a peptide comprising an elongase activity. In another embodiment, the isolated polynucleotide comprises a DNA sequence encoding a peptide consisting an elongase activity.

In another embodiment, the isolated polynucleotide comprises a DNA sequence comprising the sequence:

```
                                              (SEQ ID NO: 2)
atggcattgacggcggcctggcacaagtacgacgctatcgttagtcgc tttgttttcgatggcttgcgcagggttggcctgcaagagattcaaggc caccctcggtgatcaccgccaccttcccttcatagcctcccaacg ccacaagtgacgttcgtgctggcctatctgctgattgttgtctgcggg gttgccgctctgcgtacgagaaagtcgtccgcacctcgcgaggatccg gcgtggctgcgactgcttgtgcaagcgcacaacttggtgctaatcagc cttagcgcctacatgtcctctgccgcctgctactatgcttggaaatac ggctataggttttggggcacaaactatagccccaaggagcgggacatg ggagggctcatctataccttaacgtgtccaagctgtacgagtttgtgg
```

-continued

```
atacgctgatcatgctgctcaagggcaaggtggagcaggtttctttt tgcacgtctaccaccacgcttccatatccacgatctggtgggcaatcg catacgtcgcacctggtggtgacgcctggtactgctgcttcctgaact cgctggtccacgtactcatgtacacatactacctgcttgcgacgctgc tgggaaaggacgccaaggcgcggcgcaagtaattgtggtggggacgct acctcactcagttccagatgttccagtttgtgacgatgatgctcgagg cagcgtacacttgggcctactctccctaccccaagttttatcaaagc tgctgttcttttacatgatcactctgttggccctgtttgcaaacttct atgcacagaagcatggcagcagccgggcagccaagcaaaagctgcagt aa.
```

In another embodiment, the isolated polynucleotide comprises a DNA sequence that is at least 60% homologous to the nucleic acid sequence of SEQ ID NO: 2. In another embodiment, the isolated polynucleotide comprises a DNA sequence that is at least 70% homologous to the nucleic acid sequence of SEQ ID NO: 2. In another embodiment, the isolated polynucleotide comprises a DNA sequence that is at least 75% homologous to the nucleic acid sequence of SEQ ID NO: 2. In another embodiment, the isolated polynucleotide comprises a DNA sequence that is at least 80% homologous to the nucleic acid sequence of SEQ ID NO: 2. In another embodiment, the isolated polynucleotide comprises a DNA sequence that is at least 85% homologous to the nucleic acid sequence of SEQ ID NO: 2. In another embodiment, the isolated polynucleotide comprises a DNA sequence that is at least 90% homologous to the nucleic acid sequence of SEQ ID NO: 2. In another embodiment, the isolated polynucleotide comprises a DNA sequence that is at least 95% homologous to the nucleic acid sequence of SEQ ID NO: 2. In another embodiment, the isolated polynucleotide comprises a DNA sequence that is at least 98% homologous to the nucleic acid sequence of SEQ ID NO: 2.

In another embodiment, the isolated polynucleotide comprises a DNA sequence that is at least 60% identical to the nucleic acid sequence of SEQ ID NO: 2. In another embodiment, the isolated polynucleotide comprises a DNA sequence that is at least 70% identical to the nucleic acid sequence of SEQ ID NO: 2. In another embodiment, the isolated polynucleotide comprises a DNA sequence that is at least 75% identical to the nucleic acid sequence of SEQ ID NO: 2. In another embodiment, the isolated polynucleotide comprises a DNA sequence that is at least 80% identical to the nucleic acid sequence of SEQ ID NO: 2. In another embodiment, the isolated polynucleotide comprises a DNA sequence that is at least 85% identical to the nucleic acid sequence of SEQ ID NO: 2. In another embodiment, the isolated polynucleotide comprises a DNA sequence that is at least 90% identical to the nucleic acid sequence of SEQ ID NO: 2. In another embodiment, the isolated polynucleotide comprises a DNA sequence that is at least 95% identical to the nucleic acid sequence of SEQ ID NO: 2. In another embodiment, the isolated polynucleotide comprises a DNA sequence that is at least 98% identical to the nucleic acid sequence of SEQ ID NO: 2.

In another embodiment, the present invention provides a composition comprising the peptide as described herein. In another embodiment, the present invention provides a composition comprising the protein as described herein. In another embodiment, the present invention provides a composition comprising the polynucleotide as described herein.

In another embodiment, the present invention provides a composition comprising a vector comprising the polynucleotide as described herein. In another embodiment, one of skill in the art is able to prepare a composition comprising a peptide and/or protein as described herein. In another embodiment, one of skill in the art is able to prepare a composition comprising a polynucleotide as described herein. In another embodiment, the present invention provides a composition comprising the protein as described herein to be used in foodstuffs, dietary supplements or pharmaceutical compositions. In another embodiment, the present invention provides a composition comprising the VLC-PUFAs, the products of the elongation reaction of the protein of the present invention. In another embodiment, a composition comprising VLC-PUFAs is used in foodstuffs, dietary supplements or pharmaceutical compositions.

In another embodiment, transforming a plant with an algal-derived gene such as described herein produces better results in comparison to fungal genes. In another embodiment, P. incisa is the richest plant source of ARA. In another embodiment, an algal-derived gene such as described herein is more effective than those of other sources. In another embodiment, a DNA sequence as described herein such as but not limited to SEQ ID NO: 2 is used to engineer a transgenic organism. In another embodiment, the DNA sequence comprises the sequence shown in SEQ ID NO: 2 or variants of that sequence due, for example, to base substitutions, deletions, and/or additions. In another embodiment, the present invention provides transgenic plant oils enriched with VLCPUFA. In another embodiment, the present invention provides the reconstitution of C20-VLCPUFA biosynthesis in oil-synthesizing seeds of higher plants. In another embodiment, the present invention provides expanded use by enhancement of the levels of ARA and EPA in the transgenic plants.

In another embodiment, the present invention provides an expression vector comprising the polynucleotide as described herein. In another embodiment, the present invention provides a plant specific expression vector comprising the polynucleotide as described herein. In another embodiment, the present invention provides a cell comprising the expression vector as described herein. In another embodiment, the expression vector is contained within an agrobacterium. In another embodiment, a cell is a plant cell. In another embodiment, a plant is an oil crop. In another embodiment, the transformed plant is an oil crop.

In another embodiment, the present invention provides a transgenic plant or a transgenic seed transformed by a polynucleotide as described herein. In another embodiment, the present invention provides that the transgenic plant is a true-breeding for the polynucleotide as described herein. In another embodiment, the present invention provides a transgenic seed, produced by a transgenic plant transformed by the polynucleotide as described herein. In another embodiment, a transgenic plant or a transgenic seed as described herein produces very long-chain polyunsaturated fatty acid (VLC-PUFA). In another embodiment, a transgenic plant or a transgenic seed as described herein produces arachidonic acid.

In another embodiment, the present invention provides a method of producing very long-chain polyunsaturated fatty acid (VLC-PUFA) in a plant or a plant cell, comprising the step of transforming a plant or a plant cell with a polynucleotide as described herein. In another embodiment, a VLC-PUFA is produced from γ-linolenic acid (GLA). In another embodiment, a VLC-PUFA is produced from stearidonic acid (SDA). In another embodiment, a VLC-PUFA is produced from GLA, SDA, or their combination. In another embodiment, a VLC-PUFA comprises 20 carbons. In another embodiment, a VLC-PUFA is 20:3ω6 or 20:4ω3. In another embodiment, a VLC-PUFA is produced (elongated) by the protein as described herein in a cell or a plant. In another embodiment, a VLC-PUFA is produced (elongated) by the protein as described herein in a cell or a plant under oleogenic conditions. In another embodiment, a VLC-PUFA is produced (elongated) by the protein as described herein in a cell or a plant under nitrogen starvation conditions.

In another embodiment, the present invention provides a method of enhancing oil storage, arachidonic acid accumulation, or a combination thereof in a plant cell, comprising the step of transforming a plant cell with a polynucleotide as described herein. In another embodiment, the present invention provides a method of enhancing oil storage, arachidonic acid accumulation, or a combination thereof in a plant, comprising the step of transforming a plant with a polynucleotide as described herein. In another embodiment, the plant or plant cell is grown under nitrogen starvation conditions.

In another embodiment, the invention further provides an engineered organism, such as a transgenic plant. In another embodiment, the invention further provides an engineered organism, such as a transgenic animal. In another embodiment, an engineered organism is engineered to express a protein as described herein. In another embodiment, an engineered organism is engineered to express elevated levels of the protein. In another embodiment, an engineered plant as described herein is used for manufacturing desired PUFAs such as ARA. In another embodiment, an engineered plant as described herein is used for manufacturing desired PUFAs such as ARA at a reduced cost.

In another embodiment, an engineered organism comprises a synthetic pathway for the production of a protein. In another embodiment, an engineered organism comprising a synthetic pathway for the production of the protein allows greater control over the production of PUFAs by the pathway by an organism. In another embodiment, the pathway includes but is not limited to A'-fatty acid desaturase, and/or A'-fatty acid desaturase.

In another embodiment, an engineered plant or seed comprises an oligonucleotide as described herein. In another embodiment, an engineered plant or seed produces a protein as described herein and comprises an oligonucleotide as described herein.

In another embodiment, a PUFA is di-homo-gamma-linolenic acid, arachidonic acid, eicosapentaenoic acid, docosatrienoic acid, docosatetraenoic acid, docosapentaenoic acid or docosahexaenoic acid. In another embodiment, a PUFA is a 24 carbon fatty acid with at least 4 double bonds.

In another embodiment, expression of the protein of the invention in plants or seed requires subcloning an ORF sequence encoding the protein into a plant expression vector, which may comprise a viral 35S promoter, and a Nos terminator. In another embodiment, a cassette or promoter/coding sequence/terminator is then be subcloned into the plant binary transformation vector, and the resulting plasmid introduced into *Agrobacterium*. In another embodiment, the *Agrobacterium* strain transforms the plant. In another embodiment, the *Agrobacterium* strain transforms the plant by the vacuum-infiltration of inflorescences, and the seeds harvested and plated onto selective media containing an antibiotic. In another embodiment, the plasmid confers resistance to an antibiotic, thus only transformed plant material will grow in the presence of an antibiotic. In another embodiment, resistant lines are identified and self-fertilized to produce homozygous material. In another embodiment, leaf material is analyzed for expression of the protein comprising elongase activity.

In some embodiments, "protein" or "polypeptide" as used herein encompasses native polypeptides. (either degradation products, synthetically synthesized polypeptides or recombinant polypeptides) and peptidomimetics (typically, synthetically synthesized polypeptides), as well as peptoids and semipeptoids which are polypeptide analogs, which have, in some embodiments, modifications rendering the polypeptides even more stable while in a body or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylene bonds (—CO—CH2-). In some embodiments, the polypeptide bonds are substituted by α-aza bonds (—NH—N(R)—CO—), wherein R is any alkyl, e.g., methyl, carbo bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g., fatty acid, complex carbohydrates, etc.).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides or proteins of the present invention are utilized in therapeutics which requires the polypeptides or proteins to be in a soluble form. In some embodiments, the polypeptides or proteins of the present invention include one or more non-natural or natural polar amino acid, including but not limited to serine and threonine which are capable of increasing polypeptide or protein solubility due to their hydroxyl-containing side chain.

In some embodiments, the polypeptides or proteins of the present invention are utilized in a linear form, although it will be appreciated by one skilled in the art that in cases where cyclization does not severely interfere with polypeptide characteristics, cyclic forms of the polypeptide can also be utilized.

In some embodiments, the polypeptides or proteins of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide or protein synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides or proteins are purified by preparative high performance liquid chromatography [Creighton T. (1983) Proteins, structures and molecular principles. WH Freeman and Co. N.Y.], and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide or protein of the present invention is synthesized using a polynucleotide encoding a polypeptide or protein of the present invention. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue specific expression of the polypeptide of the present invention. In some embodiments, the cis-regulatory sequence is suitable for directing inducible expression of the polypeptide of the present invention.

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In one embodiment, following expression, the signal peptides are cleaved from the precursor proteins resulting in the mature proteins.

In some embodiments, polynucleotides of the present invention are prepared using PCR techniques or any other method or procedure known to one skilled in the art. In some embodiments, the procedure involves the legation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g., plant expression systems) to express the polypeptide of the present invention.

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In another embodiment, expression in a host cell can be accomplished in a transient or a stable fashion. In another embodiment, transient expression is from introduced constructs which contain expression signals functional in the host cell, but which constructs do not replicate and rarely integrate in the host cell, or where the host cell is not proliferating. In another embodiment, transient expression also can be accomplished by inducing the activity of a regulatable promoter operably linked to the gene of interest.

In another embodiment, stable expression is achieved by introduction of a construct that integrates into the host genome. In another embodiment, stable expression comprises autonomously replication within the host cell. In another embodiment, stable expression of the polynucleotide of the invention is selected for through the use of a selectable marker located on or transfected with the expression construct, followed by selection for cells expressing the marker. In another embodiment, stable expression results from integration, the site of the construct's integration can occur randomly within the host genome or can be targeted through the use constructs containing regions of homology with the host genome sufficient to target recombination with the host locus. In another embodiment, constructs are targeted to an endogenous locus, all or some of the transcriptional and translational regulatory regions can be provided by the endogenous locus.

In another embodiment, an expression of a protein as described herein comprising elongase activity includes functional transcriptional and translational initiation and termination regions that are operably linked to the DNA encoding the protein comprising an elongase activity. In another embodiment, transcriptional and translational initiation and termination regions are derived from a variety of nonexclusive sources, including the DNA to be expressed, genes known or suspected to be capable of expression in the desired system, expression vectors, chemical synthesis, or from an endogenous locus in a host cell. In another embodiment, expression in a plant tissue and/or plant part presents certain efficiencies, particularly where the tissue or part is one which is harvested early, such as seed, leaves, fruits, flowers, roots, etc. In another embodiment, expression can be targeted to that location in a plant by utilizing specific regulatory sequence that are known to one of skill in the art. In another embodiment, the expressed protein is an enzyme which produces a product which may be incorporated, either directly or upon further modifications, into a fluid fraction from the host plant. In another embodiment, expression of a protein of the invention, or antisense thereof, alters the levels of specific PUFAs, or derivatives thereof, found in plant parts and/or plant tissues. The elongase polypeptide coding region may be expressed either by itself or with other genes, in order to produce tissues and/or plant parts containing higher proportions of desired PUFAs or in which the PUFA composition more closely resembles that of human breast milk. In another embodiment, the termination region is derived from the 3' region of the gene from which the initiation region was obtained or from a different gene. In another embodiment, the termination region usually is selected as a matter of convenience rather than because of any particular property.

In another embodiment, a plant or plant tissue is utilized as a host or host cell, respectively, for expression of the protein of the invention which may, in turn, be utilized in the production of polyunsaturated fatty acids. In another embodiment, desired PUFAS are expressed in seed. In another embodiment, methods of isolating seed oils are known in the art. In another embodiment, seed oil components are manipulated through the expression of the protein of the invention in order to provide seed oils that can be added to nutritional compositions, pharmaceutical compositions, animal feeds and cosmetics. In another embodiment, a vector which comprises a DNA sequence encoding the protein as described herein is linked to a promoter, and is introduced into the plant tissue or plant for a time and under conditions sufficient for expression of the protein. In another embodiment, the vector comprises one or more genes that encode other enzymes, for example, elongase, Δ4-desaturase, Δ5-desaturase, Δ6-desaturase, Δ10-desaturase, Δ12-desaturase, Δ15-desaturase, Δ17-desaturase, Δ19-desaturase, or any combination thereof. In another embodiment, the plant tissue or plant produces the relevant substrate upon which the enzymes act or a vector encoding enzymes which produce such substrates may be introduced into the plant tissue, plant cell or plant. In another embodiment, a substrate is sprayed on plant tissues expressing the appropriate enzymes. In another embodiment, the invention is directed to a transgenic plant comprising the above-described vector, wherein expression of the nucleotide sequence of the vector results in production of a polyunsaturated fatty acid in, for example, the seeds of the transgenic plant.

In another embodiment, the regeneration, development, and cultivation of plants from single plant protoplast transformants or from various transformed explants is well known in the art (for example: Weissbach and Weissbach, In: Methods for Plant Molecular Biology, (Eds.), Academic Press, Inc. San Diego, Calif., (1988)). In another embodiment, regeneration and growth process comprises the steps of selection of transformed cells, culturing those individualized cells through the usual stages of embryonic development through the rooted plantlet stage. In another embodiment, transgenic embryos and seeds are similarly regenerated. In another embodiment, resulting transgenic rooted shoots are thereafter planted in an appropriate plant growth medium such as soil.

In another embodiment, development or regeneration of plants containing an exogenous polynucleotide as described herein encodes a protein as described herein and is well known in the art. In another embodiment, the regenerated plants are self-pollinated to provide homozygous transgenic plants. In another embodiment, pollen obtained from the regenerated plants is crossed to seed-grown plants of agronomically important lines. In another embodiment, pollen from plants of these important lines is used to pollinate regenerated plants. In another embodiment, a transgenic plant of the present invention containing a desired polypeptide is cultivated using methods well known to one skilled in the art.

In another embodiment, a variety of methods for the regeneration of plants from plant tissue. In another embodiment, the method of regeneration will depend on the starting plant tissue and the particular plant species to be regenerated. In another embodiment, methods for transforming dicots, primarily by use of *Agrobacterium tumefaciens*, and obtaining transgenic plants are known in the art McCabe et al., Biol. Technology 6:923 (1988), Christou et al., Plant Physiol. 87:671-674 (1988)); Cheng et al., Plant Cell Rep. 15:653657 (1996), McKently et al., Plant Cell Rep. 14:699-703 (1995)); Grant et al., Plant Cell Rep. 15:254-258, (1995).

In another embodiment, transformation of monocotyledons using electroporation, particle bombardment, and *Agrobacterium* are known. In another embodiment, transformation and plant regeneration are well established in the art. In another embodiment, assays for gene expression based on the transient expression of cloned nucleic acid constructs have been developed by introducing the nucleic acid molecules into plant cells by polyethylene glycol treatment, electroporation, or particle bombardment (Marcotte et al., Nature 335: 454-457 (1988); Marcotte et al., Plant Cell 1:523-532 (1989); McCarty et al., Cell 66:895-905 (1991); Hattori et al., Genes Dev. 6:609-618 (1992); Goff et al., EMBO J. 9:2517-2522 (1990)).

In another embodiment, transient expression systems are used to functionally dissect the oligonucleotides constructs. In another embodiment, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing. DNA, 2, Cold Spring Harbor, N.Y. (1998); Plant Molecular Biology: A Laboratory Manual, eds. Clark, Springer, N.Y. (1997)).

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, expression vectors containing regulatory elements from eukaryotic viruses such as retroviruses are used by the present invention. In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus, and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., *Science* 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide or protein), the expression construct of the present invention can also include sequences engineered to optimize stability, production, purification, yield or activity of the expressed polypeptide or protein.

In some embodiments, transformed cells are cultured under effective conditions, which allow for the expression of high amounts of recombinant polypeptide or protein. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide or protein of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides or proteins of the present invention either remain within the recombinant cell, secreted into the fermentation medium, secreted into a space between two cellular membranes, or retained on the outer surface of a cell or viral membrane.

In one embodiment, following a predetermined time in culture, recovery of the recombinant polypeptide or protein is effected.

In one embodiment, the phrase "recovering the recombinant polypeptide or protein" used herein refers to collecting the whole fermentation medium containing the polypeptide or protein and need not imply additional steps of separation or purification.

In one embodiment, polypeptides or proteins of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide or proteins of the present invention and fused cleavable moiety. In one embodiment, a fusion protein can be designed so that the polypeptide or protein can be readily isolated by affinity chromatography; e.g., by immobilization on a column specific for the cleavable moiety. In one embodiment, a cleavage site is engineered between the polypeptide or protein and the cleavable moiety and the polypeptide or protein can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide or protein of the present invention is retrieved in "substantially pure" form.

In one embodiment, the phrase "substantially pure" refers to a purity that allows for the effective use of the protein in the applications described herein.

In one embodiment, the polypeptide or protein of the present invention can also be synthesized using in vitro expression systems. In one embodiment, in vitro synthesis methods are well known in the art and the components of the system are commercially available.

In another embodiment, the invention comprises a process for making a very long-chain polyunsaturated fatty acid produced by the protein of the invention (the elongase) in a cell as described herein. In another embodiment, a very long-chain polyunsaturated fatty acid produced by the protein of the invention is utilized as a food additive. In another embodiment, a very long-chain polyunsaturated fatty acid produced by the protein of the invention is utilized as a supplement. In another embodiment, a very long-chain polyunsaturated fatty acid produced by the protein of the invention is administered to a human subject. In another embodiment, a very long-chain polyunsaturated fatty acid produced by the protein of the invention is administered to a baby. In another embodiment, a very long-chain polyunsaturated fatty acid produced by the protein of the invention is administered to an infant. In another embodiment, a very long-chain polyunsaturated fatty acid produced by the protein of the invention is administered to an animal. In another embodiment, a very long-chain polyunsaturated fatty acid produced by the protein of the invention is administered to a mammal. In another embodiment, a very long-chain polyunsaturated fatty acid produced by the protein of the invention is administered to a farm animal, a rodent, a pet, or a lab animal.

In another embodiment, the described pharmaceutical and nutritional compositions are utilized in connection with animals (i.e., domestic or non-domestic), as well as humans, as animals experience many of the same needs and conditions as humans. For example, the oil or acids of the present invention may be utilized in animal or aquaculture feed supplements, animal feed substitutes, animal vitamins or in animal topical ointments.

In another embodiment, a very long-chain polyunsaturated fatty acid produced by the protein of the invention is utilized in an infant formula. In another embodiment, a very long-chain polyunsaturated fatty acid produced by the protein of the invention is administered to a subject having a deficiency in very long-chain polyunsaturated fatty acid. In another embodiment, a very long-chain polyunsaturated fatty acid is a polyunsaturated C20 fatty acid.

In another embodiment, the isolated protein comprising elongase activity is used indirectly or directly in the production of polyunsaturated fatty acids. In another embodiment, "Directly" is meant to encompass the situation where the enzyme directly converts the acid to another acid. In another embodiment, the latter of which is utilized in a composition (e.g., the conversion of linoleic acid (LA) to eicosadienoic acid (EDA)). In another embodiment, "Indirectly" is meant to encompass the situation where an acid is converted to another acid (i.e., a pathway intermediate) by the enzyme (e.g., LA to EDA) and then the latter acid is converted to another acid by use of a non-elongase enzyme. In another embodiment, a very long-chain polyunsaturated fatty acid produced either directly or indirectly is added to a nutritional composition, pharmaceutical compositions, cosmetics, and animal feeds, all of which are encompassed by the present invention.

In another embodiment, nutritional compositions include any food or preparation for human or animal consumption including for enteral or parenteral consumption, which when taken into the body (a) serve to nourish or build up tissues or supply energy and/or (b) maintain, restore or support adequate nutritional status or metabolic functions. In another embodiment, the nutritional composition of the present invention comprises at least one oil or acid produced directly or indirectly by use of the protein of the invention and may either be in a solid or liquid form. In another embodiment, the composition includes edible macronutrients, vitamins and minerals in amounts desired for a particular use. In another embodiment, the amount of such ingredients will vary depending on whether the composition is intended for use with normal, healthy infants, children or adults having specialized needs such as those which accompany certain metabolic conditions (e.g., metabolic disorders).

In another embodiment, the macronutrients include edible fats, carbohydrates and proteins. In another embodiment, edible fats include but are not limited to coconut oil, soy oil, and mono- and diglycerides. In another embodiment, carbohydrates include but are not limited to glucose, edible lactose and hydrolyzed search. In another embodiment, proteins which are utilized in the nutritional composition of the invention include but are not limited to soy proteins, electrodialysed whey, electrodialysed skim milk, milk whey, or the hydrolysates of these proteins.

In another embodiment, vitamins and minerals are added to the nutritional compositions of the present invention and include but are not limited to: calcium, phosphorus, potassium, sodium, chloride, magnesium, manganese, iron, copper, zinc, selenium, iodine, and Vitamins A, E, D, C, and the B complex. Other such vitamins and minerals may also be added.

In another embodiment, components utilized in the nutritional compositions of the present invention will be of semi-purified or purified origin. By semi-purified or purified is meant a material which has been prepared by purification of a natural material or by synthesis. In another embodiment, a nutritional compositions of the present invention include but are not limited to infant formulas, dietary supplements, dietary substitutes, and rehydration compositions. In another embodiment, a nutritional composition of the present invention may also be added to food even when supplementation of the diet is not required. In another embodiment, a composition is added to food of any type including but not limited to margarines, modified butters, cheeses, milk, yogurt, chocolate, candy, snacks, salad oils, cooking oils, cooking fats, meats, fish and beverages.

In another embodiment, a nutritional composition is an enteral nutritional product. In another embodiment, a nutritional composition is an adult or pediatric enteral nutritional product. In another embodiment, a composition is administered to adults or children experiencing stress or having specialized needs due to chronic or acute disease states. In another embodiment, a composition comprises, in addition to polyunsaturated fatty acids produced in accordance with the present invention, macronutrients, vitamins and minerals as described above. In another embodiment, the macronutrients may be present in amounts equivalent to those present in human milk or on an energy basis, i.e., on a per calorie basis.

In another embodiment, the present invention includes an enteral formula comprising polyunsaturated fatty acids produced in accordance with the present invention. In another embodiment, an enteral formula is sterilized and subsequently utilized on a ready-to-feed basis or stored in a concentrated liquid or powder. In another embodiment, a powder is prepared by spray drying the formula prepared as indicated above, and reconstituting it by rehydrating the concentrate. In another embodiment, the present invention includes an adult and pediatric nutritional formulas. In another embodiment, adult and pediatric nutritional formulas are known in the art and are commercially available (e.g., Similac®, Ensure®, Jevity® and Alimentum® from Ross Products Division, Abbott Laboratories). In another embodiment, an oil or acid produce in accordance with the present invention may be add to any of these formulas.

In another embodiment, a nutritional formula comprises macronutrients, vitamins, and minerals, as provided herein, in addition to the PUFAs produced in accordance with the present invention. In another embodiment, the presence of additional components helps the individual ingest the minimum daily requirements of these elements. In another embodiment, an adult and pediatric nutritional formulas comprises the PUFAs as described herein and zinc, copper, folic acid and antioxidants, or any combination thereof. In another embodiment, PUFAs produced in accordance with the present invention, or derivatives thereof, are added to a dietary substitute or supplement, particularly an infant formula, for patients undergoing intravenous feeding or for preventing or treating malnutrition or other conditions or disease states. In another embodiment, PUFAs produced in accordance with the present invention are used to alter, the composition of infant formulas in order to better replicate the PUFA content of human breast milk or to alter the presence of PUFAs normally found in a non-human mammal's milk.

In another embodiment, parenteral nutritional compositions comprising from about 2 to about 30 weight percent fatty acids calculated as triglycerides are encompassed by the present invention. In another embodiment, other vitamins, particularly fat-soluble vitamins such as vitamin A, D, E and L-carnitine are also included. In another embodiment, a preservative such as alpha-tocopherol is added in an amount of about 0.05-0.5% by weight.

In another embodiment, the present invention includes a PUFA produced in accordance with the present invention or host cells containing them, used as animal food supplements to alter an animal's tissue or milk fatty acid composition to one more desirable for human or animal consumption.

In one embodiment, the polypeptides or protein of the present invention can be provided to the individual per se. In one embodiment, the polypeptides or proteins of the present invention can be provided to the individual as part of a pharmaceutical composition where it is mixed with a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism. In one embodiment, "active ingredient" refers to the polypeptide or protein sequence of interest.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents, which increase the solubility of the active ingredients to allow for the preparation of highly concentrated solutions.

In another embodiment, the proteins as described herein can be delivered in a vesicle, in particular a liposome (see Langer, *Science* 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (*Science* 249:1527-1533 (1990)).

In some embodiments, the protein as described herein is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In some embodiments, pharmaceutical compositions suitable for use in context of the present invention include compositions wherein the proteins or oligonucleotides are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., aspartame, citric acid), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g., Avicel™, RC-591), tragacanth and sodium alginate; typical wetting agents include lecithin and polyethylene oxide sorbitan (e.g., polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the proteins or oligonucleotides of the invention into or onto particulate preparations of polymeric compounds such as polylactic acid, polglycolic acid, hydrogels, etc., or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the proteins or oligonucleotides of the invention coupled to antibodies directed against tissue-specific receptors, ligands or antigens or coupled to ligands of tissue-specific receptors.

In some embodiments, the proteins or oligonucleotides of the invention modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified proteins or oligonucleotides of the invention exhibit substantially longer half-lives in blood following intravenous injection than do the corresponding unmodified compounds. In one embodiment, modifications also increase the proteins or oligonucleotides solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the proteins or oligonucleotides of the invention described herein is determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the polypeptides or proteins of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Experimental Procedures

Growth Conditions

Axenic cultures of *P. incisa* were cultivated on BG-11 nutrient medium in 250 ml Erlenmeyer glass flasks in an incubator shaker under an air/$CO_2$ atmosphere (99:1, v/v), controlled temperature (25° C.) and illumination (115 μmol quanta $m^{-2}$ $s^{-1}$) at a speed of 170 rpm. For nitrogen starvation experiments, cells of daily-diluted cultures were collected by centrifugation, washed thrice in sterile DDW and resuspended in 100 ml of nitrogen-free BG11 medium. Cultures were further grown at the same conditions for 14 d. To prepare nitrogen-free medium, $NaNO_3$ was omitted from the BG-11 medium and ferric ammonium citrate was substituted with ferric citrate.

RNA Isolation

Cells for RNA isolation were harvested from 50 ml log phase culture (Time 0) grown in complete BG11 and cultured on nitrogen-free medium for 3, 7 and 14 days. The cultures were filtered through a glass fiber paper filter (GF-52, Schleicher & Schuell, Germany), cells were collected by scraping and immediately flash-frozen in liquid nitrogen and stored at −80° C. for further use. Total RNA was isolated either using the RNeasy Plant Mini kit (Qiagen, Hilden, Germany) or by the procedure described by Bekisieva et al., with minor modifications. Three independent RNA isolations were conducted for each growth period. For real-time PCR studies, the total RNA samples were further treated with RNAase-free DNAase (Epicentre, Madison, Wis.).

Construction of Subtracted cDNA Library

The subtracted complementary DNA (cDNA) library was prepared from cDNAs enriched for differentially expressed sequences obtained from *P. incisa* cultures in the log phase (driver) and after 3 days of nitrogen starvation (tester), using a PCR-Select™ cDNA Subtraction Kit (Clontech, Mountain View, Calif.). First, a double-stranded cDNA was synthesized from total RNA isolated from cells during log phase and N-starvation and digested with RsaI. Subtraction was then done in both directions: to enrich for "log phase" cDNAs, the cDNA sequences of N-starved cells were subtracted from those of log phase cells; conversely, to enrich for cDNAs of N-starved cells, log phase cDNA sequences were subtracted from those of N-starved cells. Two portions of the tester cDNA were ligated to adaptor primers. After two cycles of hybridization with excess of driver over tester, the ends of the enriched tester cDNA population were filled in by DNA polymerase and selectively amplified by PCR. Following a subsequent PCR with nested primers, the two differentially expressed cDNA populations were cloned into a pGEM-T vector (Promega, Madison, Wis.) to produce clones of the subtracted libraries. Plasmids were sequenced by an ABI automated sequencer. Among the 56 differentially expressed sequence tags (ESTs) clones, one was found to be highly similar to PUFA elongases.

Generation of 5' and 3' End Fragments of the Putative *P. Incisa* PUFA Elongase

To generate the full-length cDNA of the putative PUFA elongase, 3'- and 5'-rapid amplification of the cDNA ends (RACE) was performed using a BD Smart™ RACE cDNA Amplification Kit (BD Biosciences Clontech, Foster City, Calif.) according to the manufacturer's manual. To amplify the 5'-end, the reverse gene-specific primers (GSP) 5'-CCCG-GCTGCTGCCATGCTTCTGTG (EL5R1) (SEQ ID NO: 3) 5'-TGGGGTAGGGAGAGTAGGCCCAAGT (EL5RN) (SEQ ID NO: 4) were designed using the Primer3 online software. Based on the nucleotide sequence of the obtained 5'-end fragment, two forward GSPs, 5'-GCCTACATGTC-CTCTGCCGCCTGCTA (EL3R1) (SEQ ID NO: 5) and the nested, 5'-GCGGGACATGGGAGGGCTCATCTATACC (EL3R2) (SEQ ID NO: 6), were constructed to amplify the 3'-end of the target gene. RACE PCR reactions were conducted using 5' and 3'-RACE-Ready cDNAs made from 1 µg total RNA of N-starved cells with 50×BD Advantage 2 polymerase mix (Clontech Laboratories Inc., Mountain View, Calif.). The PCR products of the expected size were excised and purified from the gel (NucleoSpin Extract II purification kit, Machery-Nagel, Duren, Germany) and ligated into a pGEM T-Easy vector (Promega, Madison, Wis.). The full length cDNA corresponding to the *P. incisa* putative PUFA elongase (designated PiELO1) was assembled from the 5' and 3' RACE fragments and its ORF was further subcloned into a pYES2 vector (Invitrogen, Carlsbad, Calif.).

Expression and Functional Characterization of PiELO1 cDNA in the Yeast *Saccharomyces Cerevisiae*

The ORF encoding for PiELO1 was amplified using PfuUltra II fusion HS DNA polymerase (Stratagene, La Jolla, Calif.) with the forward primer, 5'-AGGAATTCAAAATGGCATTGACGGCGGCCT (PUFAEL5RES1) (SEQ ID NO: 7), containing a restriction site (underlined) and a yeast translation consensus followed by ATG (bold) and the reverse primer 5'-CATTCTAGATTACTGCAGCTTTTGCTTGGCTGC (PUFAEL3RES2) (SEQ ID NO: 8) containing a restriction site (underlined) and a stop codon (bold). The amplified sequence was then restricted with EcoRI and XbaI (NEB, Ipswich, Mass.). The expected bands were gel-purified with NucleoSpin Extract II purification kit (Machery-Nagel GmbH, Duren, Germany) and ligated into a EcoRI-XbaI cut pYES2 vector, yielding YpPiELO1. *Saccharomyces cerevisiae* strain W303 was transformed with YpPiELO1 by the PEG/lithium acetate method. The yeast cells harboring the empty pYES2 vector were used as control. Transformants were selected by uracil prototrophy on yeast synthetic medium (YSM) lacking uracil (Invitrogen, Carlsbad, Calif.). For functional expression, a minimal selection medium containing 2% (w/v) raffinose was inoculated with the YpPiELO1 transformants and grown at 27° C. for 24 h in a water bath shaker. Five ml of sterile YSM, containing 1% (w/v) Tergitol-40 and 250 µM of the appropriate fatty acid was inoculated with raffinose-grown cultures to obtain an OD of 0.2 at 600 nm. Expression was induced by adding galactose to a final concentration of 2% (w/v) and cultures were further grown at 27° C. for 48 h. Cells were harvested by centrifugation, washed twice with 0.1% $NaHCO_3$, freeze-dried and used for fatty acid analysis.

Fatty Acid Analysis

Fatty acid methyl esters (FAMEs) were obtained by transmethylation of the freeze-dried yeast or *P. incisa* cells, with dry methanol containing 2% (v/v) $H_2SO_4$ and heating at 80° C. for 1.5 h while stirring under an argon atmosphere. Gas chromatographic (GC) analysis of FAMEs was performed on a Thermo Ultra Gas chromatograph (Thermo Scientific, Italy) equipped with. PTV injector, FID detector and a fused silica capillary column (30 m×0.32 mm; ZB WAXplus, Phenomenex). FAMEs were identified by co-chromatography with authentic standards (Sigma Chemical Co., St. Louis, Mo.) and FAME of fish oil (Larodan Fine Chemicals, Sweden). Each sample was analyzed in duplicates.

Real-Time Quantitative RT-PCR

Template cDNA for real-time quantitative PCR (RTQPCR) was synthesized using 1 µg of total RNA in a total volume of 20-µL, using random decamers (Reverse-iT™ $1^{st}$ Strand Synthesis Kit, ABgene, Surrey, UK). Each 20-µL cDNA reaction was then diluted 3-fold with PCR grade water.

Primer Design and Validation

Real-Time Quantitative PCR primer pairs were designed for the PiELO1 and the house keeping gene 18S SSU rRNA using the PrimerQuest tool. Parameters were set for a primer length of 19 to 26 bp, primer melting temperature of 60.0±1.0° C., and amplicon length of 90 to 150. Primer pairs were validated using seven serial fifty-fold dilutions of cDNA samples and standard curves were plotted to test for linearity of the response. The primer pairs and primer concentrations with reaction efficiencies of 100±10% were chosen for quantitative RT-PCR analysis of relative gene expression. The nucleotide sequences and characteristics of primers used for quantitative RT-PCR analysis are presented in Table 1.

TABLE 1

Parameters of the primers used in RTQPCR reactions

| Gene | Forward primer<br>Reverse primer | Amplicon size (bp) | PCR efficiency (%) |
|---|---|---|---|
| PiELO1 | AAGCTGTACGAGTTTGTGGATACGCT<br>(SEQ ID NO: 9)<br>GGATATGGAAGCGTGGTGGTAGA<br>(SEQ ID NO:10) | 95 | 92.3 |
| 18S SSU rRNA | TGAAAGACGAACTTCTGCGAAAGCA<br>(SEQ ID NO: 11)<br>AGTCGGCATCGTTTATGGTTGAGA<br>(SEQ ID NO: 12) | 120 | 96.8 |

Gene Expression Profiling

Gene expression profiling was done by real-time quantitative PCR using duplicate reactions for each sample of three independent RNA isolations with a gene-specific primer pair using Absolute™ Blue QPCR SYBR Green ROX Mix (AB-gene, Surrey, UK) in a Real-Time PCR 7500 system (Applied Biosystems). The amplification protocol was 50° C. for 2 min, 95° C. for 15 min, 40 cycles of 95° C. for 15 s and 60° C. for 1 min. A dissociation curve was obtained for each pair of primers to confirm that a single, specific product was produced in each reaction.

Calculation of Gene Transcript Levels

The mean fold changes in gene expression were calculated according to the $2^{-\Delta\Delta C_t}$ method using the average of threshold cycle (Ct) values from triplicate cDNA-primer samples. The ΔCt followed by the ΔΔCt was calculated from the average Ct values of the target and the endogenous genes. The transcript abundance of the PiELO1 gene was normalized to the endogenous control 18S SSU rRNA gene. The fold-change in gene expression was calculated using $2^{-\Delta\Delta C_t}$ to find the expression level of the target gene which was normalized to the endogenous gene, relative to the expression of the target gene at time 0.

Example 1

Identification and Characterization of PiELO1

The BLASTX analysis of clones obtained through subtractive hybridization revealed a clone of 141 bp whose putative amino acid sequence was highly homological to the C-terminal region of PUFA elongases. Using GSP primers, the 870 bp 5'-end fragment was amplified and the sequence information was used to obtain the 3' end fragment from the 3' RACE Ready cDNA. Alignment of the 800 bp 3'-end sequence with that of the 5'-end fragment provided an overlapping nucleotide sequence and included the partial 141 bp sequence, thus confirming the amplification of both ends of the expected gene. The assembled complete 867 bp cDNA sequence, designated as PiELO1, preceded and followed by 22 and 150 bp nucleotides at 5' and 3' UTR, respectively. PiELO1 contained an ORF of 289 predicted amino acid residues consistent with functionally characterized PUFA elongase ORFs from fungi, lower plants and algae (FIG. 1). The deduced amino acid sequence of the PiELO1 was 50% identical to O. tauri and M. polymorpha Δ6 PUFA elongase, while sharing 48 and 44% identity with P. patens Δ6 elongase and M. polymorpha Δ5 elongase, respectively. The PiELO1 is also similar, yet with a lower score, to Δ6 elongases of fungal origin. It shares 40 and 36% identity with the Δ6 PUFA elongases of Thraustochytrium and M. alpina (not included in the alignment), respectively.

The predicted amino acid sequence of the PiELO1 contained four conserved motifs that are characteristic for PUFA elongases (FIG. 1, highlighted). The hydropathy plot of the PiELO1 deduced amino acid sequences was obtained using the algorithm available in the DAS transmembrane prediction server. The two strictly hydrophobic transmembrane domains were found about 50 amino acids downstream and upstream from the N and C termini, respectively, while the two less hydrophobic domains were located about 100 amino acids downstream and upstream from the N and C termini, respectively (FIG. 2).

Example 2

Phylogenetic Analysis

An unrooted phylogenetic tree of the PiELO1 and several functionally characterized PUFA elongases was constructed to identify their functional and phylogenetic relationships by the neighbor-joining program in MEGA4. According to FIG. 3 one can see that PiELO1 falls into a group of PUFA elongases of lower eukaryotes. Although the group contains mostly PUFA elongases with Δ6 activity, some Δ5 elongases, e.g., that of M. polymorpha and Leishmania infantum, are more related to Δ6 elongases of lower eukaryotes than to Δ5 elongases of higher eukaryotes. PiELO1 makes a closely related subgroup with OtELO1, MpELO1, MpELO2 and PpELO1, the OtELO1 being the closest one.

Functional Expression of PiELO1 in S. Cerevisiae

Figure 4:
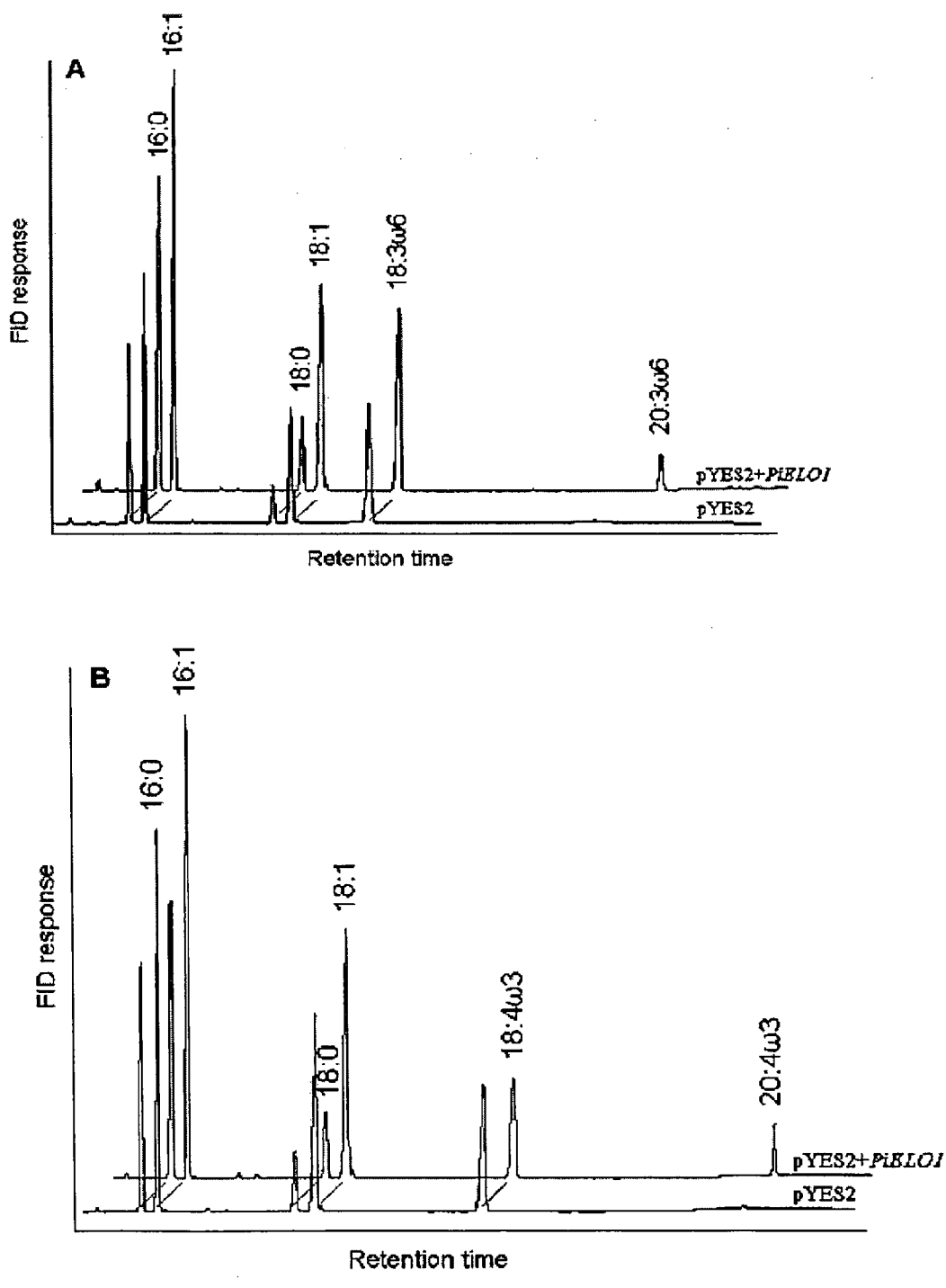
FIG. 4. Is a GC of FAMEs of recombinant yeast harboring pYES2 and PiELO1 fed with 18:3ω6 (A) and 18:4ω3 (B) CONTROL.

To characterize the enzymatic activity of PiELO1, the pYES2 plasmid containing the PiELO1 ORF downstream of the GAL1 promoter was transformed into S. cerevisiae. The PiELO1 was expressed in the presence of the Δ6 PUFA elongase substrates, 18:3ω6 (γ-linolenic acid, GLA) and 18:4ω3 (stearidonic acid, STA). GC analysis of the FAMEs of transformed yeast cells showed that PiELO1 elongated GLA and STA, converting them into dihomo-γ-linoleic acid (DGLA, 20:3ω6) and eicosatetraenoic acid (20:4ω3), respectively (FIG. 4). The yeast cells harboring the empty vector alone did not demonstrate any elongation activity on the added substrates, confirming that the PiELO1 encoded enzyme has a Δ6 PUFA elongase activity. Feeding the PiELO1 transformants with the ω6 fatty acids, LA and ARA, did not result in their elongation (not shown).

Figure 5:
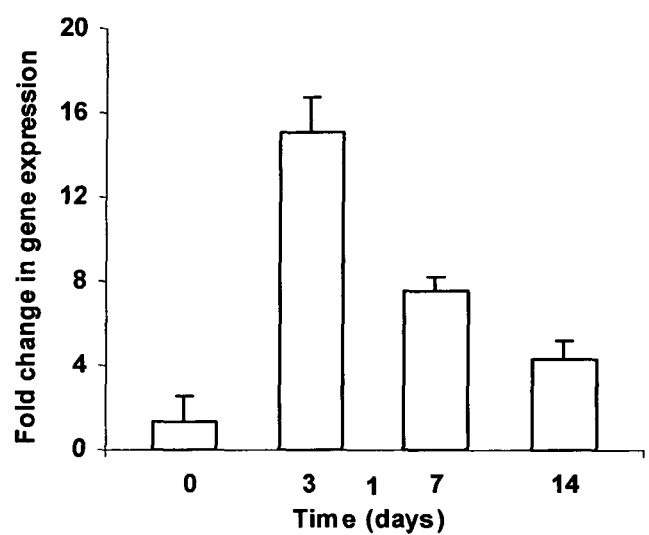
FIG. 5. Summarizes the results of quantitative Real-time RT-PCR analysis of PiELO1 gene expression in log phase (Time 0) and N-starved (3, 7 & 14 d) cells of *P. incisa*. The transcript abundance of the gene was normalized to 18S SSU rRNA gene.

Real-time quantitative PCR was performed to quantitate the alterations in expression levels of the Δ6 PiELO1 in P. incisa cells under nitrogen starvation. The expression levels of the genes under nitrogen starvation were measured and normalized to the expression level of the endogenous control gene 18S SSU rRNA. The fold change in the expression level of the target genes in P. incisa cells grown for 3, 7 and 14 d on N-free medium was calculated relative to the expression level of the target genes in the log phase (time 0). The results showed that during nitrogen starvation the mRNA of the PiELO1 gene was induced to its highest level at day 3 (14 fold increase over time 0), decreasing thereafter to a level still higher than that of day 0 (FIG. 5). After 7 and 14 d, expression level of the PiELO1 gene was still 7.5 and 4.3 fold higher, respectively. The level of expression of the PiELO1 gene correlated with the increase in the share of ARA and the C20/(C16+C18) elongation ratio (Table 2). The share of the elongation product, DGLA, increased sharply at day 3 (50% increase over time 0) and decreased thereafter.

TABLE 2

Major fatty acid composition of P. incisa cells grown under N-starvation

| Time (days) | Fatty acid composition (% of total fatty acids) | | | | | | | | | | | | |
|---|---|---|---|---|---|---|---|---|---|---|---|---|---|
| | 16:0 | 16:1 | 16:2 | 16:3 | 18:0 | 18:1 | 18:2 | 18:3 ω6 | 18:3 ω3 | 20:3 ω6 | 20:4 ω6 | 20:5 ω3 | Elo. ratio[a] |
| 0 | 19.1 | 5.6 | 4.1 | 2.9 | 3.1 | 9.1 | 20.1 | 1.2 | 6.0 | 0.5 | 23.0 | 0.7 | 0.34 |
| 3 | 12.7 | 2.3 | 1.5 | 1.9 | 3.8 | 15.2 | 13.5 | 1.6 | 2.0 | 0.9 | 39.7 | 0.6 | 0.74 |

TABLE 2-continued

Major fatty acid composition of *P. incisa* cells grown under N-starvation

| Time (days) | Fatty acid composition (% of total fatty acids) | | | | | | | | | | | | |
|---|---|---|---|---|---|---|---|---|---|---|---|---|---|
| | 16:0 | 16:1 | 16:2 | 16:3 | 18:0 | 18:1 | 18:2 | 18:3 ω6 | 18:3 ω3 | 20:3 ω6 | 20:4 ω6 | 20:5 ω3 | Elo. ratio[a] |
| 7 | 10.7 | 1.0 | 0.6 | 1.1 | 3.5 | 14.9 | 10.0 | 1.1 | 0.9 | 1.0 | 50.0 | 0.5 | 1.10 |
| 14 | 9.0 | 0.2 | 0.3 | 0.8 | 3.1 | 13.4 | 8.8 | 0.9 | 0.6 | 0.9 | 56.9 | 0.6 | 1.44 |

[a]Elongation ratio, C20/(C18 + C16)

Many microalgae produce VLC-PUFAs of nutritional, pharmaceutical and industrial importance. In most microalgal species the VLC-PUFAs are restricted to membranal lipids. In contrast, in *P. incisa*, over 95% of cell AA is deposited in TAG in cytoplasmic oil bodies. Recent successes in the production of VLC-PUFA by genetically modified oil plants has elicited further investigations concerning the role and regulation of the genes and enzymes involved in VLC-PUFA biosynthesis. The conversion of GLA into DGLA by the PUFA elongase was found to be the rate-limiting step in the biosynthesis of ARA in *M. alpina*.

A cDNA (PiELO1) of an elongase encoding for a deduced protein was isolated from *P. incisa*, structurally similar to Δ6 PUFA elongase gene products from microalgae, lower plants and fungi (FIG. 1). The deduced amino acid sequence of the PiElO1 ORF was about 50% identical to that of Δ6 elongases from the liverwort *M. polymorpha* (AAT85662), the green marine microalga *O. tauri* (AAV67797) and the moss *P. patens* (AAL84174). In similarity to recently cloned PUFA elongases, the predicted protein is highly hydrophobic and has two strongly hydrophobic transmembrane regions, the first one located about 50 amino acids downstream of the N-terminus and the second one in the vicinity of the C-terminus. The PiELO1 sequence was identified in a C-terminal lysine-rich motif, important for the endoplamic reticulum targeting, as well as four conserved motifs FYxSKxxEFxDT (SEQ ID NO: 13), QxxxLHVYHHxxI (SEQ ID NO: 14), NSxxH-VxMYxYY (SEQ ID NO: 15) and TxxQxxQF (SEQ ID NO: 16), including a highly conserved histidine box suggested to be functionally important for PUFA elongation (FIG. 1). These conserved motifs were not found in other classes of plant microsomal elongases, .beta. ketoacyl CoA synthases and fatty acid elongases (FAE) involved in extraplastidial elongation of saturated and monounsaturated fatty acids. A variant histidine box QAFHH with three replacements in C18-Δ9-PUFA elongase IgASE1 from *I. galbana* is thought to be important for enzymatic activity rather then for substrate specificity.

PiELO1 is another example of a single step Δ6 PUFA elongases cloned from an algal species. Similarly to GLELO of *M. alpina*, PiELO1 prefers the Δ6 C18 PUFA substrates, GLA and STA. Only these Δ6 fatty acids were, when exogenously added, elongated to the respective products by *S. cerevisiae* cells transformed with PiELO1 (FIG. 4). Transformation of a higher plant so as to render it to produce Δ6 PUFA requires that the elongase used will have a high selectivity for Δ6 PUFA, thereby reducing the appearance of side products in the transformed plant. Bifunctional invertebrate PUFA elongases with both Δ6 and Δ5 activities (OmELO, XiELO, and CiELO) are less desirable in plant transformations.

Figure 3:
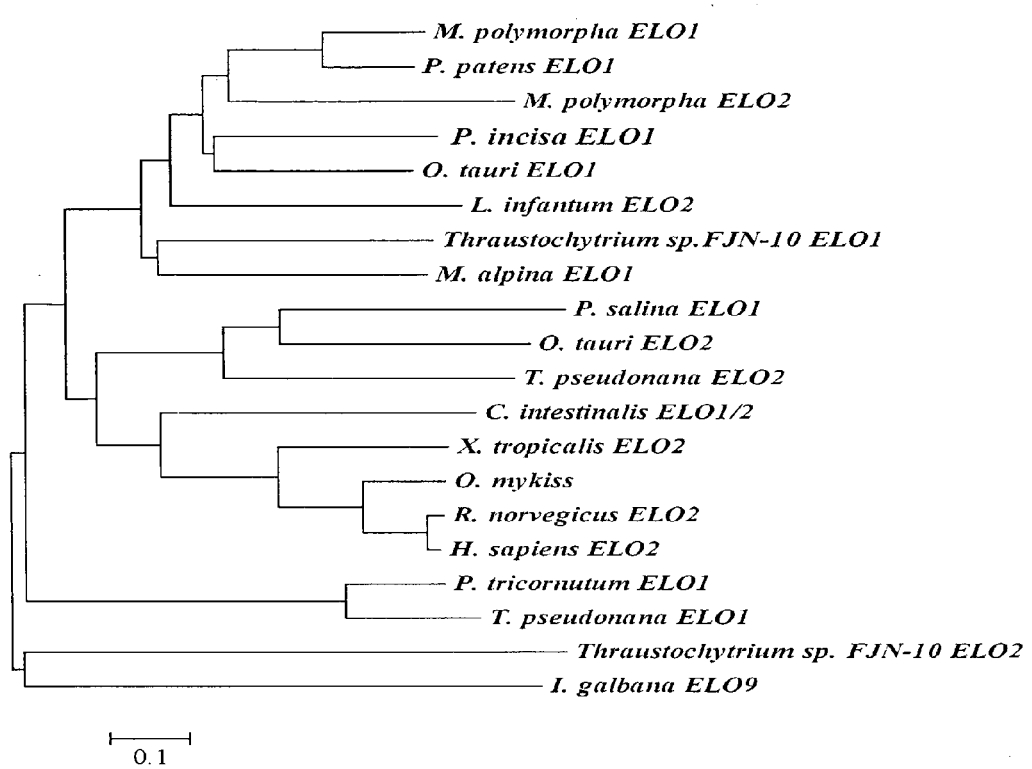
FIG. 3. Is an unrooted phylogram of PiELO1 and some other functionally characterized PUFA elongases. The alignment was generated by the CLUSTAL W program and the unrooted phylogram was constructed by the neighbor-joining method using the MEGA4 software. GeneBank accession numbers for the PUFA elongases are: ACK99719 (Δ6, *P. incisa*), AAV67797 (Δ6, *O. tauri*), AAV67798 (Δ5, *O. tauri*), AAT85662 (Δ6, *M. polymorpha*), BAE71129 (Δ5, *M. polymorpha*), AAL84174 (Δ6, *P. patens*), CAJ30819 (Δ6, *Thraustochytrium* sp.), CAM55873 (Δ5, *Thraustochytrium* sp.), AAF70417 (Δ6, *M. alpina*), XP_001467802 (*L. infantum*), AAV67803 (Δ6/Δ5, *O. mykiss*), NP_001029014 (Δ6/Δ5, *C. intestinalis*), NP_068586 (Δ6/Δ5, *H. sapiens*), AAY15135 (Δ5, *P. salina*), CAM55851 (Δ6 *P. tricornutum*), AAL37626 (Δ9, *I. galbana*), AAV67799 (Δ6, *T. pseudonana*), AAV67800 (Δ5, *T. pseudonana*), CAA92958 (Δ6, *C. elegans*), NP_599209 (Δ6/Δ5, *R. norvegicus*).

Phylogenetic analysis showed (FIG. 2) that the PUFA elongases are not strictly divided according to their substrate specificity. The Δ6 elongases of algal (OtELO1, TpELO1, PiELO1) and moss (PpELO1) origin are functionally restricted to the elongation of Δ6-C18-PUFAs, however these elongases are placed in separate groups on the phylogenetic tree (FIG. 3). PiELO1 is closely related to OtELO1 isolated from a chloropyte and a lower plant rather than to ELO1 genes isolated from a diatom, although both are specific for the elongation of Δ6-C18-PUFAs (FIG. 3). PiELO1 is highly similar to and is placed in the same group with both Δ6 and Δ5 elongases of the liverwort *M. polymorpha*. Kajikawa et al. suggested that MpELO2, a Δ5 elongase, is likely to have originated through gene duplication of the MpELO1 gene. The algal Δ5 PUFA elongases, OtELO2, TpELO2 and the *P. salina* ELO1 are more likely to share a common branch with the mammalian and animal Δ5 PUFA elongases, OmELO and HsELO2, while they are also similar to bifunctional PUFA elongases such as CiELO1/2.

Quantitative real time PCR studies revealed that the expression level of the PiELO1 gene was up regulated during the time course of N-starvation (FIG. 5). Nitrogen starvation led to a continuous increase in the share of ARA and the C20/(C16+C18) elongation ratio (Table 2). However, a major transcriptional activation of PiELO1 which occurred on day 3 (14-fold increase in transcript level) coincided with the steep rise in AA accumulation and elongation ratio (Table 2). The increase in PiELO1 transcription level followed by enhanced biosynthesis of ARA may be interpreted as an increase in PiELO1 enzyme level and/or enzymatic activity. The importance of the transcriptional activation of PiELO1 is supported by the fact that PUFA elongase was the only ARA biosynthesis related gene that was obtained from the subtractive library. The significance of the coordinated transcription and action of desaturases and elongases in ARA biosynthesis in *P. incisa* is yet to be elucidated. Possibly, the elongation of GLA by PiELO1 could be rate-limiting in ARA biosynthesis as it is in *M. alpina*. Abbadi et al. (2004) speculated that in transgenic plants modified with VLC-PUFA biosynthesis genes, substrate availability rather than enzymatic activity is rate-limiting in the Δ6 elongation of PUFA.

In conclusion, the PiELO1 is a Δ6 PUFA elongase, specifically elongating GLA and SDA to 20:3ω6 and 20:4ω3, respectively. The PiELO1 gene is upregulated under oleogenic conditions. This gene is a likely candidate for genetic transformations of oil seed plants that will enable the production of VLC-PUFAs in the transgenic plants. The upregulation of the PiELO1 gene under nitrogen starvation conditions must have significant physiological importance for adaptation of *P. incisa* cells to nitrogen deficiency.

What is claimed is:

1. A composition comprising an isolated protein having the amino acid sequence set forth in SEQ ID NO: 1 and a synthetic carrier.
2. A composition comprising an isolated protein having the amino acid sequence set forth in SEQ ID NO: 1, wherein said composition is an infant formula.
3. An isolated complementary DNA (cDNA) molecule encoding the protein of SEQ ID NO: 1.
4. An isolated polynucleotide comprising the nucleic acid sequence set forth in SEQ ID NO: 2.
5. An expression vector comprising a polynucleotide encoding the protein of SEQ ID NO: 1 and further comprising a heterologous regulatory element.
6. A cell comprising the expression vector of claim 5.
7. The cell of claim 5, wherein said cell is a plant cell.
8. A composition comprising the expression vector of claim 5.
9. A transgenic plant or a transgenic seed transformed by a polynucleotide encoding the protein of SEQ ID NO: 1.
10. The transgenic plant of claim 9, wherein said plant is true-breeding for said polynucleotide encoding the protein of SEQ ID NO: 1.
11. A transgenic seed, produced by a transgenic plant transformed by a polynucleotide encoding the protein of SEQ ID NO: 1.
12. The transgenic plant or a transgenic seed of claim 9, producing very long-chain polyunsaturated fatty acid (VLC-PUFA).
13. The transgenic plant or a transgenic seed of claim 12, wherein said VLC-PUFA is arachidonic acid.
14. A method of producing very long-chain polyunsaturated fatty acid (VLC-PUFA) in a plant or a plant cell, comprising the step of transforming a plant or a plant cell with a polynucleotide encoding the protein of SEQ ID NO: 1, thereby producing a VLC-PUFA in a plant or a plant cell.
15. The method of claim 14, wherein said plant or said plant cell comprises γ-linolenic acid (GLA), stearidonic acid (SDA), or their combination.
16. The method of claim 14, wherein said VLC-PUFA is 20:3ω6 or 20:4ω3.
17. The method of claim 14, wherein said plant or said plant cell is grown under oleogenic conditions.
18. The method of claim 14, wherein said plant or said plant cell is grown under nitrogen starvation conditions.
19. A method of enhancing oil storage, arachidonic acid accumulation, or a combination thereof in a plant cell, comprising the step of transforming said plant cell with a polynucleotide encoding the protein of SEQ ID NO: 1, thereby enhancing oil storage, arachidonic acid accumulation, or a combination thereof in a plant cell.

20. The method of claim 19, wherein said plant cell is grown under nitrogen starvation conditions.

* * * * *

SEQUENCE LISTING

<160> NUMBER OF SEQ ID NOS: 18

<210> SEQ ID NO 1
<211> LENGTH: 288
<212> TYPE: PRT
<213> ORGANISM: Prostanthera incisa

<400> SEQUENCE: 1

Met Ala Leu Thr Ala Ala Trp His Lys Tyr Asp Ala Ile Val Ser Arg
1               5                   10                  15

Phe Val Phe Asp Gly Leu Arg Arg Val Gly Leu Gln Glu Ile Gln Gly
            20                  25                  30

His Pro Ser Val Ile Thr Ala His Leu Pro Phe Ile Ala Ser Pro Thr
        35                  40                  45

Pro Gln Val Thr Phe Val Leu Ala Tyr Leu Leu Ile Val Val Cys Gly
    50                  55                  60

Val Ala Ala Leu Arg Thr Arg Lys Ser Ser Ala Pro Arg Glu Asp Pro
65                  70                  75                  80

Ala Trp Leu Arg Leu Leu Val Gln Ala His Asn Leu Val Leu Ile Ser
                85                  90                  95

Leu Ser Ala Tyr Met Ser Ser Ala Ala Cys Tyr Tyr Ala Trp Lys Tyr
            100                 105                 110

Gly Tyr Arg Phe Trp Gly Thr Asn Tyr Ser Pro Lys Glu Arg Asp Met
        115                 120                 125

Gly Gly Leu Ile Tyr Thr Phe Tyr Val Ser Lys Leu Tyr Glu Phe Val
    130                 135                 140

Asp Thr Leu Ile Met Leu Leu Lys Gly Lys Val Glu Gln Val Ser Phe
145                 150                 155                 160

Leu His Val Tyr His His Ala Ser Ile Ser Thr Ile Trp Trp Ala Ile
                165                 170                 175

Ala Tyr Val Ala Pro Gly Gly Asp Ala Trp Tyr Cys Cys Phe Leu Asn
            180                 185                 190

Ser Leu Val His Val Leu Met Tyr Thr Tyr Tyr Leu Leu Ala Thr Leu
        195                 200                 205

Leu Gly Lys Asp Ala Lys Ala Arg Arg Lys Tyr Leu Trp Trp Gly Arg
    210                 215                 220

Tyr Leu Thr Gln Phe Gln Met Phe Gln Phe Val Thr Met Met Leu Glu
225                 230                 235                 240

Ala Ala Tyr Thr Trp Ala Tyr Ser Pro Tyr Pro Lys Phe Leu Ser Lys
                245                 250                 255

Leu Leu Phe Phe Tyr Met Ile Thr Leu Leu Ala Leu Phe Ala Asn Phe
            260                 265                 270

Tyr Ala Gln Lys His Gly Ser Ser Arg Ala Ala Lys Gln Lys Leu Gln
        275                 280                 285

<210> SEQ ID NO 2
<211> LENGTH: 867
<212> TYPE: DNA
<213> ORGANISM: Prostanthera incisa

<400> SEQUENCE: 2
atggcattga cggcggcctg gcacaagtac gacgctatcg ttagtcgctt tgttttcgat      60
ggcttgcgca gggttggcct gcaagagatt caaggccacc cctcggtgat caccgcccac     120
cttcccttca tagcctcccc aacgccacaa gtgacgttcg tgctggccta tctgctgatt     180
gttgtctgcg gggttgccgc tctgcgtacg agaaagtcgt ccgcacctcg cgaggatccg     240

```
gcgtggctgc gactgcttgt gcaagcgcac aacttggtgc taatcagcct tagcgcctac    300
atgtcctctg ccgcctgcta ctatgcttgg aaatacggct ataggttttg gggcacaaac    360
tatagcccca aggagcggga catgggaggg ctcatctata ccttttacgt gtccaagctg    420
tacgagtttg tggatacgct gatcatgctg ctcaagggca aggtggagca ggtttctttt    480
ttgcacgtct accaccacgc ttccatatcc acgatctggt gggcaatcgc atacgtcgca    540
cctggtggtg acgcctggta ctgctgcttc ctgaactcgc tggtccacgt actcatgtac    600
acatactacc tgcttgcgac gctgctggga aaggacgcca aggcgcggcg caagtatttg    660
tggtggggac gctacctcac tcagttccag atgttccagt ttgtgacgat gatgctcgag    720
gcagcgtaca cttgggccta ctctccctac cccaagtttt tatcaaagct gctgttcttt    780
tacatgatca ctctgttggc cctgtttgca aacttctatg cacagaagca tggcagcagc    840
cgggcagcca agcaaaagct gcagtaa                                        867
```

```
<210> SEQ ID NO 3
<211> LENGTH: 24
<212> TYPE: DNA
<213> ORGANISM: Artificial sequence
<220> FEATURE:
<223> OTHER INFORMATION: the reverse gene-specific primers (GSP) primer

<400> SEQUENCE: 3
cccggctgct gccatgcttc tgtg                                           24

<210> SEQ ID NO 4
<211> LENGTH: 25
<212> TYPE: DNA
<213> ORGANISM: Artificial sequence
<220> FEATURE:
<223> OTHER INFORMATION: reverse gene-specific primer

<400> SEQUENCE: 4
tggggtaggg agagtaggcc caagt                                          25

<210> SEQ ID NO 5
<211> LENGTH: 26
<212> TYPE: DNA
<213> ORGANISM: Artificial sequence
<220> FEATURE:
<223> OTHER INFORMATION: forward GSP primer

<400> SEQUENCE: 5
gcctacatgt cctctgccgc ctgcta                                         26

<210> SEQ ID NO 6
<211> LENGTH: 28
<212> TYPE: DNA
<213> ORGANISM: Artificial sequence
<220> FEATURE:
<223> OTHER INFORMATION: forward GSP primer

<400> SEQUENCE: 6
gcgggacatg ggagggctca tctatacc                                       28

<210> SEQ ID NO 7
<211> LENGTH: 30
<212> TYPE: DNA
<213> ORGANISM: Artificial sequence
<220> FEATURE:
<223> OTHER INFORMATION: forward primer PUFAEL5RES1
```

-continued

<400> SEQUENCE: 7
aggaattcaa aatggcattg acggcggcct                                30

<210> SEQ ID NO 8
<211> LENGTH: 33
<212> TYPE: DNA
<213> ORGANISM: Artificial sequence
<220> FEATURE:
<223> OTHER INFORMATION: PUFAEL3RES2

<400> SEQUENCE: 8
cattctagat tactgcagct tttgcttggc tgc                             33

<210> SEQ ID NO 9
<211> LENGTH: 26
<212> TYPE: DNA
<213> ORGANISM: Artificial sequence
<220> FEATURE:
<223> OTHER INFORMATION: Reverse primer PiELO1

<400> SEQUENCE: 9
aagctgtacg agtttgtgga tacgct                                     26

<210> SEQ ID NO 10
<211> LENGTH: 23
<212> TYPE: DNA
<213> ORGANISM: Artificial sequence
<220> FEATURE:
<223> OTHER INFORMATION: Reverse primer PiELO1

<400> SEQUENCE: 10
ggatatggaa gcgtggtggt aga                                        23

<210> SEQ ID NO 11
<211> LENGTH: 25
<212> TYPE: DNA
<213> ORGANISM: Artificial sequence
<220> FEATURE:
<223> OTHER INFORMATION: Forward primer 18S SSU rRNA

<400> SEQUENCE: 11
tgaaagacga acttctgcga aagca                                      25

<210> SEQ ID NO 12
<211> LENGTH: 24
<212> TYPE: DNA
<213> ORGANISM: Artificial sequence
<220> FEATURE:
<223> OTHER INFORMATION: Reverse primer 18S SSU rRNA

<400> SEQUENCE: 12
agtcggcatc gtttatggtt gaga                                       24

<210> SEQ ID NO 13
<211> LENGTH: 12
<212> TYPE: PRT
<213> ORGANISM: Artificial sequence
<220> FEATURE:
<223> OTHER INFORMATION: conserved motives
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

```
<220> FEATURE:
<221> NAME/KEY: misc_feature
<222> LOCATION: (10)..(10)
<223> OTHER INFORMATION: Xaa can be any naturally occurring amino acid

<400> SEQUENCE: 13

Phe Tyr Xaa Ser Lys Xaa Xaa Glu Phe Xaa Asp Thr
1               5                   10

<210> SEQ ID NO 14
<211> LENGTH: 13
<212> TYPE: PRT
<213> ORGANISM: Artificial sequence
<220> FEATURE:
<223> OTHER INFORMATION: conserved motives of PiELO1
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 14

Gln Xaa Xaa Xaa Leu His Val Tyr His His Xaa Xaa Ile
1               5                   10

<210> SEQ ID NO 15
<211> LENGTH: 12
<212> TYPE: PRT
<213> ORGANISM: Artificial sequence
<220> FEATURE:
<223> OTHER INFORMATION: Derived from PiELO1 P. Incisa
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 15

Asn Ser Xaa Xaa His Val Xaa Met Tyr Xaa Tyr Tyr
1               5                   10

<210> SEQ ID NO 16
<211> LENGTH: 8
<212> TYPE: PRT
<213> ORGANISM: Artificial sequence
<220> FEATURE:
<223> OTHER INFORMATION: Derived from PiELO1 P. Incisa
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 16

Thr Xaa Xaa Gln Xaa Xaa Gln Phe
1               5

<210> SEQ ID NO 17
```

-continued

```
<211> LENGTH: 289
<212> TYPE: PRT
<213> ORGANISM: Myremecia

<400> SEQUENCE: 17

Met Ala Leu Thr Ala Ala Trp His Lys Tyr Asp Ala Ile Val Ser Arg
1               5                   10                  15

Phe Val Phe Asp Gly Leu Arg Arg Val Gly Leu Gln Glu Ile Gln Gly
            20                  25                  30

His Pro Ser Val Ile Thr Ala His Leu Pro Phe Ile Ala Ala Ser Pro
        35                  40                  45

Thr Pro Gln Val Thr Phe Val Leu Ala Tyr Leu Leu Ile Val Val Cys
    50                  55                  60

Gly Val Ala Ala Leu Arg Thr Arg Lys Ser Ser Ala Pro Arg Glu Asp
65                  70                  75                  80

Pro Ala Trp Leu Arg Leu Leu Val Gln Ala His Asn Leu Val Leu Ile
                85                  90                  95

Ser Leu Ser Ala Tyr Met Ser Ser Ala Ala Cys Tyr Tyr Ala Trp Lys
            100                 105                 110

Tyr Gly Tyr Arg Phe Trp Gly Thr Asn Tyr Ser Pro Lys Glu Arg Asp
        115                 120                 125

Met Gly Gly Leu Ile Tyr Thr Leu Tyr Val Ser Lys Leu Tyr Glu Phe
    130                 135                 140

Val Asp Thr Leu Ile Asn Leu Leu Lys Gly Lys Val Glu Gln Val Ser
145                 150                 155                 160

Phe Leu His Val Tyr His His Ala Ser Ile Ser Thr Ile Trp Trp Ala
                165                 170                 175

Ile Ala Tyr Val Ala Pro Gly Gly Val Ala Trp Tyr Cys Cys Phe Leu
            180                 185                 190

Asn Ser Pro Val His Val Leu Met Tyr Thr Tyr Tyr Leu Ala Ala Thr
        195                 200                 205

Leu Leu Gly Lys Asp Ala Lys Ala Arg Arg Lys Tyr Leu Trp Trp Gly
    210                 215                 220

Arg Thr Leu Thr Gln Phe Gln Met Gly Gln Phe Val Thr Met Met Leu
225                 230                 235                 240

Glu Ala Ala Tyr Thr Trp Ala Tyr Ser Pro Tyr Pro Lys Phe Leu Ser
                245                 250                 255

Lys Leu Leu Phe Phe Tyr Asn Ile Thr Leu Leu Ala Leu Phe Ala Asn
            260                 265                 270

Phe Tyr Ala Gln Lys His Gly Ser Ser Arg Ala Ala Lys Gln Lys Pro
        275                 280                 285

Gln

<210> SEQ ID NO 18
<211> LENGTH: 289
<212> TYPE: PRT
<213> ORGANISM: Parietochloris

<400> SEQUENCE: 18

Met Ala Leu Thr Ala Ala Trp His Lys Tyr Asp Ala Ile Val Ser Arg
1               5                   10                  15

Phe Val Phe Asp Gly Leu Arg Arg Val Gly Leu Gln Glu Ile Gln Gly
            20                  25                  30

His Pro Ser Val Ile Thr Ala His Leu Pro Phe Ile Ala Ala Ser Pro
        35                  40                  45
```

-continued

```
Thr Pro Gln Val Thr Phe Val Leu Ala Tyr Leu Leu Ile Val Val Cys
    50                  55                  60

Gly Val Ala Ala Leu Arg Thr Arg Lys Ser Ser Ala Pro Arg Glu Asp
65              70                  75                      80

Pro Ala Trp Leu Arg Leu Leu Val Gln Ala His Asn Leu Val Leu Ile
                85                  90                  95

Ser Leu Ser Ala Tyr Met Ser Ser Ala Ala Cys Tyr Tyr Ala Trp Lys
            100                 105                 110

Tyr Gly Tyr Arg Phe Trp Gly Thr Asn Tyr Ser Pro Lys Glu Arg Asp
            115                 120                 125

Met Gly Gly Leu Ile Tyr Thr Phe Tyr Val Ser Lys Leu Tyr Glu Phe
            130                 135                 140

Val Asp Thr Leu Ile Asn Leu Leu Lys Gly Lys Val Glu Gln Val Ser
145                 150                 155                 160

Phe Leu His Val Tyr His His Ala Ser Ile Ser Thr Ile Trp Trp Ala
                165                 170                 175

Ile Ala Tyr Val Ala Pro Gly Gly Val Ala Trp Tyr Cys Cys Phe Leu
                180                 185                 190

Asn Ser Leu Val His Val Leu Met Tyr Thr Tyr Tyr Leu Ala Ala Thr
            195                 200                 205

Leu Leu Gly Lys Asp Ala Lys Ala Arg Arg Lys Tyr Leu Trp Trp Gly
        210                 215                 220

Arg Tyr Leu Thr Gln Phe Gln Met Gly Gln Phe Val Thr Met Met Leu
225                 230                 235                 240

Glu Ala Ala Tyr Thr Trp Ala Tyr Ser Pro Tyr Pro Lys Phe Leu Ser
                245                 250                 255

Lys Leu Leu Phe Phe Tyr Asn Ile Thr Leu Leu Ala Leu Phe Ala Asn
            260                 265                 270

Phe Tyr Ala Gln Lys His Gly Ser Ser Arg Ala Ala Lys Gln Lys Leu
        275                 280                 285

Gln
```